United States Patent
Enoki et al.

(10) Patent No.: US 6,531,148 B1
(45) Date of Patent: Mar. 11, 2003

(54) THERAPEUTIC AGENTS

(75) Inventors: Tatsuji Enoki, Otsu (JP); Jun Tomono, Muko (JP); Nobuto Koyama, Uji (JP); Katsushige Ikai, Koka-gun (JP); Hiroaki Sagawa, Kusatsu (JP); Ikunoshin Kato, Uji (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/719,314

(22) PCT Filed: Jun. 8, 1999

(86) PCT No.: PCT/JP99/03058

§ 371 (c)(1),
(2), (4) Date: Feb. 1, 2001

(87) PCT Pub. No.: WO99/64424

PCT Pub. Date: Dec. 16, 1999

(30) Foreign Application Priority Data

| Jun. 9, 1998 | (JP) | 10/175295 |
| Jul. 24, 1998 | (JP) | 10/223723 |
| Jan. 20, 1999 | (JP) | 10/011639 |

(51) Int. Cl.⁷ .............................................. A61K 47/00
(52) U.S. Cl. ..................... 424/439; 424/400; 424/464; 424/489; 514/25; 536/4.1
(58) Field of Search .................. 536/4.1; 514/25; 424/400, 439, 464, 489

(56) References Cited

U.S. PATENT DOCUMENTS

| 5,380,834 A | 1/1995 | Mizukoshi et al. |
| 5,691,341 A | * 11/1997 | Nakai et al. ............... 514/249 |
| 2002/0016299 A1 | * 2/2002 | Sakai et al. .................. 514/23 |

FOREIGN PATENT DOCUMENTS

| JP | 6-80565 A | 3/1994 |
| JP | 6-182965 A | 7/1994 |

* cited by examiner

*Primary Examiner*—Thurman K. Page
*Assistant Examiner*—Charesse Evans
(74) *Attorney, Agent, or Firm*—Browdy and Neimark, P.L.L.C.

(57) ABSTRACT

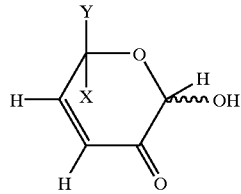

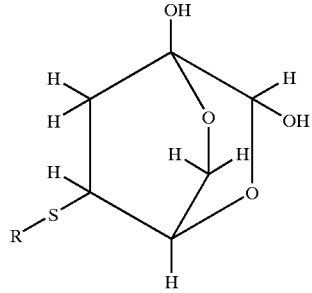

Therapeutic or preventive agents for diseases requiring apoptosis induction, cancerous diseases, diseases requiring the inhibition of active oxygen production, those requiring the inhibition of nitrogen monoxide production, those requiring the inhibition of prostaglandin synthesis, those requiring the inhibition of synovial cell proliferation, those requiring the induction of heat shock protein production or those requiring the inhibition of α-glycosidase, which contain as the active ingredient compounds selected from among compounds represented by general formula (I), (wherein X and Y are each H or $CH_2OH$, provided that when X is $CH_2OH$, Y is H, while when X is H, Y is $CH_2OH$), those represented by general formula (II), (wherein R is a residue obtained by freeing a compound having an SH group from the SH group) and salts of both; and foods, drinks, cosmetics and so on, containing compounds selected from among compounds of general formula (I), those of general formula (II) and salts of both.

23 Claims, 10 Drawing Sheets

THERAPEUTIC AGENTS

The present application is the national stage under 35 U.S.C. 371 of PCT/JP99/03058, filed Jun. 8, 1999.

TECHNICAL FIELD

The present invention relates to utilization of a physiologically active substance derived from a naturally occurring material. More specifically, it relates to the physiologically active substance, a method for producing the substance, a pharmaceutical composition, a food or a drink, an antioxidant composition, a composition for preserving freshness and a cosmetic composition that contains the physiologically active substance as an active ingredient.

BACKGROUND ART

Recently, attention has drawn to a mode of death of cells or tissues which is called as apoptosis (self-blasting or self-destruction of cells).

The apoptosis is a death that has been originally programmed in the genome of a cell, and is different from necrosis, which is a pathological cell death. Specifically, it is considered that the following processes lead to the death. The activation of a gene that programs the apoptosis triggered by certain external or internal factor(s) causes the biosynthesis of a programmed death protein. In some cases, a programmed death protein that exists in a cell in its inactive form becomes activated. The thus generated active programmed death protein destroys the cell.

Induction of the apoptosis in desired tissues or cells is very worthwhile because it makes it possible to eliminate unnecessary or harmful cells from a living body in a natural manner.

OBJECT OF INVENTION

The main object of the present invention is to provide a highly safe substance having a physiological function such as an apoptosis-inducing activity derived from a naturally occurring material, as well as a method for producing and use of the substance.

SUMMARY OF INVENTION

The present invention is outlined as follows. The first aspect of the present invention relates to a pharmaceutical composition which contains as an active ingredient a compound selected from the group consisting of:

a compound of formula (I):

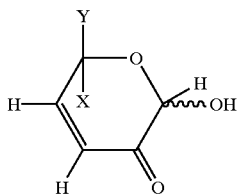

(I)

wherein X and Y are H or $CH_2OH$, provided that when X is $CH_2OH$, Y is H, while when X is H, Y is $CH_2OH$;

a compound of formula (II):

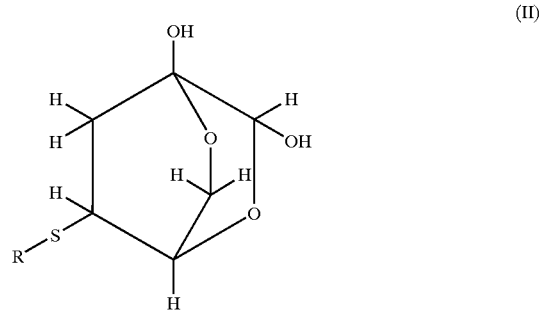

(II)

wherein R is a residue obtained by freeing an SH group from an SH group-containing compound; and salts thereof, said composition being used for treating or preventing a disease that requires induction of apoptosis for its treatment or prevention, a cancerous disease, a disease that requires inhibition of active oxygen production for its treatment or prevention, a disease that requires inhibition of nitrogen monoxide production for its treatment or prevention, a disease that requires inhibition of prostaglandin synthesis for its treatment or prevention, a disease that requires inhibition of synovial cell proliferation for its treatment or prevention, a disease that requires induction of heat shock protein production for its treatment or prevention, or a disease that requires inhibition of α-glycosidase for its treatment or prevention.

The second aspect of the present invention relates to a method for producing a compound of formula (I), characterized in that the method comprises treating 3,6-anhydrogalactose and/or a compound having 3,6-anhydrogalactose at its reducing end under neutral to alkaline conditions.

The third aspect of the present invention relates to a compound of formula (II) or a salt thereof.

The fourth aspect of the present invention relates to a method for producing a compound of formula (II), characterized in that the method comprises reacting a compound of formula (I) with an SH group-containing compound.

The fifth aspect of the present invention relates to a food or a drink which contains, which is produced by diluting, and/or which is produced by adding thereto a compound selected from the group consisting of a compound of formula (I), a compound of formula (II) and salts thereof.

The sixth aspect of the present invention relates to a food or a drink which contains, which is produced by diluting, and/or which is produced by adding thereto a compound of formula (I) obtained by treating 3,6-anhydrogalactose and/or a compound having 3,6-anhydrogalactose at its reducing end under neutral to alkaline conditions.

The seventh aspect of the present invention relates to an antioxidant composition which contains as an active ingredient a compound selected from the group consisting of a compound of formula (I), a compound of formula (II) and salts thereof.

The eighth aspect of the present invention relates to a food or a drink which contains the antioxidant composition of the seventh aspect of the present invention.

The ninth aspect of the present invention relates to a compound for antioxidation of formula (I) or formula (II). For example, the compound can be used, without limitation, as a compound for inhibiting active oxygen production.

The tenth aspect of the present invention relates to a composition for preserving freshness which contains as an active ingredient a compound selected from the group consisting of a compound of formula (I), a compound of formula (II) and salts thereof.

The eleventh aspect of the present invention relates to a cosmetic composition which contains as an active ingredient a compound selected from the group consisting of a compound of formula (I), a compound of formula (II) and salts.

The twelfth aspect of the present invention relates to a composition for inhibiting α-glycosidase which contains as an active ingredient a compound selected from the group consisting of a compound of formula (I), a compound of formula (II) and salts thereof.

The thirteenth aspect of the present invention relates to an apoptosis-inducing substance produced by treating 3,6-anhydrogalactose and/or a compound having 3,6-anhydrogalactose at its reducing end under neutral to alkaline conditions.

The fourteenth aspect of the present invention relates to a food or a drink which contains, which is produced by diluting, and/or which is produced by adding thereto an apoptosis-inducing substance produced by treating 3,6-anhydrogalactose and/or a compound having 3,6-anhydrogalactose at its reducing end under neutral to alkaline conditions.

Hereinafter, the present invention will be explained in detail with reference to the attached drawings.

DETAILED DESCRIPTION OF THE INVENTION

Figure 1:
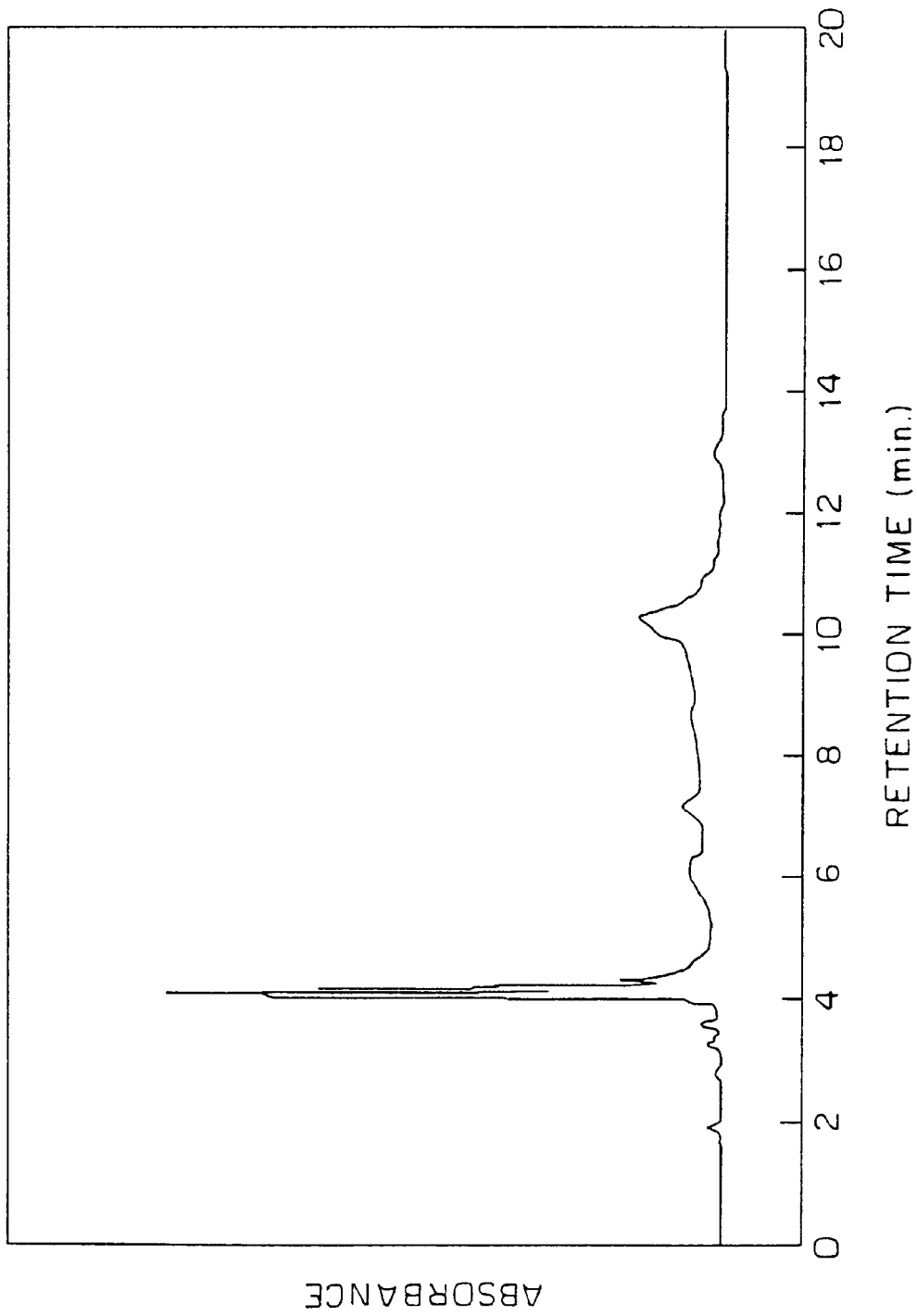
FIG. 1 illustrates the normal phase HPLC chromatogram of Sample 2.

As used herein, 3,6-anhydrogalactose means 3,6-anhydrogalactopyranose of formula (III):

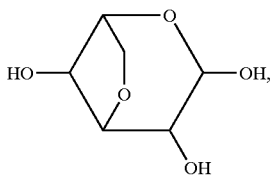

(III)

an aldehyde thereof of formula (IV):

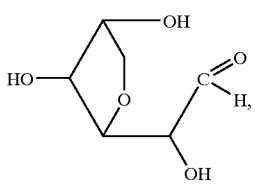

(IV)

or a hydrate thereof of formula (V):

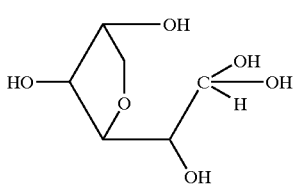

(V)

In addition, it includes a sulfated derivative and a methylated derivative thereof. The structures of the compounds represented by formulas (III) to (V) may be represented by using different expression forms. It is intended that the compounds of formulas (III) to (V) include compounds represented by such different expression forms and their possible tautomers. In addition, the configuration of formulas (III) to (V) is not limited to specific one as long as a desired activity is exerted. The D-form or L-form, or a mixture thereof may be used.

For example, a compound having 3,6-anhydrogalactose at its reducing end can be obtained, without limitation, by hydrolysis under acidic conditions below pH 7 and/or enzymatic digestion of a 3,6-anhydrogalactose-containing material in the present invention. Alternatively, it can be chemically synthesized.

The compounds having 3,6-anhydrogalactose preferably used in the present invention include, for example, a soluble saccharide whose non-reducing end is a sugar other than L-galactose-6-sulfate such as an oligosaccharide other than agarobiose and κ-carabiose having agarobiose, κ-carabiose or 3,6-anhydrogalactose at its reducing end. An agarooligosaccharide, i.e., a saccharide whose non-reducing end is L-galactose, is very suitable for a prodrug.

Examples of the 3,6-anhydrogalactose-containing materials of the present invention include, but are not limited to, viscous polysaccharides from red algae such as agar, agarose, agaropectin, funoran, porphyran, carrageenan, furcellaran and hypnean [Kyoritsu-shuppan Inc., "Tatouseika-gaku 1—Kagakuhen—(Biochemistry of Polysaccharides 1—Chemistry—), pp. 314 (1969)]. The 3,6-anhydrogalactose-containing materials used in the present invention also include materials that contain these polysaccharides.

For example, red algae belonging to Gelidiaceae such as *Gelidium amansii, Gelidium japonicum, Gelidium pacificum, Gelidium subcostatum, Pterocladia tenuis* and

*Acanthopeltis japonica*, red algae belonging to Gracilariaceae such as *Gracilaria verrucosa* and *Gracilaria gigas*, red algae belonging to Ceramiaceae such as *Ceramium kondoi* and *Campylaephora hypnaeoides*, as well as other red algae are used as raw materials for agarose and agaropectin. Usually, several kinds of algae are used in combination as the raw materials. Gelidium jelly is obtained by extracting raw material algae with hot water and then cooling the extract. Agar is obtained by removing water from the gelidium jelly by freeze-dehydration or compression-dehydration and drying it. Agar normally contains about 70% of agarose and about 30% of agaropectin. The agar can be further purified to prepare agarose with high purity.

The 3,6-anhydrogalactose-containing materials used in the present invention include the above-mentioned raw material algae for agar, gelidium jelly, agar, purified agarose, purified agaropectin and intermediate products or by-products that are obtained during the production of these substances.

Usually, algae dried in the sun are used as the raw materials. Both of fresh algae and dried algae can be used in the present invention. Algae that are bleached while spraying water during the drying, so-called bleached raw algae, can also be used. Agar in various forms including bar, belt, board, thread and powder can be used regardless of the source algae. Purified agarose with low purity or high purity having various agarose contents can be used.

Agarose is a polysaccharide that has a principal structure in which D-galactose and 3,6-anhydro-L-galactose are alternately linked together. In the structure, the 1-position of D-galactose is linked to the 4-position of 3,6-anhydro-L-galactose through a β-glycoside bond, and the 1-position of 3,6-anhydro-L-galactose is linked to the 3-position of D-galactose through an α-glycoside bond. The α-1,3-bond is selectively hydrolyzed by mild hydrolysis with a dilute acid or α-agarase [Carbohydr. Res., 66: 207 (1978)]. The β-1,4-bond is selectively hydrolyzed by β-agarase.

Carrageenan is a polysaccharide that is contained in red algae belonging to Gigartinaceae, Solieriaceae, Hypneaceae and the like. κ-Carrageenan, λ-carrageenan and η-carrageenan are known. κ-Carrageenan has a basic structure in which the 1-position of D-galactose-4-sulfate is linked to the 4-position of 3,6-anhydro-D-galactose through a β-glycoside bond, the 1-postion of 3,6-anhydro-D-galactose is linked to the 3-position of D-galactose-4-sulfate through an α-glycoside bond, and they are repeated alternately. λ-Carrageenan has a basic structure in which the 1-position of D-galactose is linked to the 4-position of D-galactose-2,6-disulfate through a β-glycoside bond, the 1-position of D-galactose-2,6-disulfate is linked to the 3-position of D-galactose through an α-glycoside bond, and they are repeated alternately. Carrageenan is utilized as a gelling agent for foods.

A product of partial decomposition of the 3,6-anhydrogalactose-containing material obtained by chemical, physical and/or enzymatic means can be also used a 3,6-anhydrogalactose-containing material in the present invention. Furthermore, a compound having 3,6-anhydrogalactose at its reducing end can be prepared by partial decomposition of a 3,6-anhydrogalactose-containing material by chemical, physical and/or enzymatic means.

A purified, partially purified or crude material containing a compound having 3,6-anhydrogalactose at its reducing end may be used in the present invention depending on the purpose.

Examples of means of chemical decomposition of the 3,6-anhydrogalactose-containing material include hydrolysis under acidic conditions below pH 7. Examples of means of physical decomposition include radiation of electromagnetic waves or ultrasonic waves. Examples of means of enzymatic digestion include hydrolysis with a hydrolase such as agarase and carrageenase.

The conditions used for the decomposition of a 3,6-anhydrogalactose-containing material under acidic conditions below pH 7 are not limited to specific one as long as the decomposition produces a compound having 3,6-anhydrogalactose at its reducing end such as a compound other than agarobiose and κ-carabiose having agarobiose, κ-carabiose or 3,6-anhydrogalactose at its reducing end.

For example, a compound having 3,6-anhydrogalactose at its reducing end is produced by dissolving or suspending a 3,6-anhydrogalactose-containing material in an acid at a concentration of 0.0001 to 5 N and reacting the mixture for a few seconds to a few days. The reaction time required for the production of the compound having 3,6-anhydrogalactose at its reducing end is shortened by heating the mixture during the reaction.

Any acid can used to dissolve or suspend a 3,6-anhydrogalactose-containing material. Inorganic acids such as hydrochloric acid, sulphuric acid and nitric acid as well as organic acids such as citric acid, formic acid, acetic acid, lactic acid and ascorbic acid can be used. The acid can be used at a concentration of, without limitation, 0.0001 to 5 N, preferably 0.001 to 1 N. In addition, the reaction may be carried out, without limitation, at a temperature of 0 to 200° C., preferably 20 to 130° C. Furthermore, the reaction may be carried out, without limitation, for a few seconds to a few days. The acid and the concentration thereof, and the temperature and time of the reaction may be suitable selected. Such selection depends on the following: the 3,6-anhydrogalactose-containing material used as the raw material such as agarose or carrageenan; the yield of the compound having 3,6-anhydrogalactose at its reducing end of interest such as agarobiose and κ-carabiose and a compound other than agarobiose and κ-carabiose having 3,6-anhydrogalactose at its reducing end; and the degree of polymerization of the compound other than agarobiose and κ-carabiose having 3,6-anhydrogalactose at its reducing end of interest. In general, the acid decomposition reaction proceeds more rapidly by selecting a strong acid rather than a weak acid, a high acid concentration rather than a low acid concentration, and a high temperature rather than a low temperature.

For example, an acid decomposition product obtained by suspending agar in 0.1 N HCl at a concentration of 10% by weight and dissolving the agar by heating at 100° C. for 13 minutes does not gelate any longer even if the solution is cooled to its freezing point. When the saccharides contained in the solution are analyzed with gel filtration HPLC, normal phase HPLC and the like, saccharides with high molecular weight are scarcely observed and most of the saccharides are found to be decomposed to soluble saccharides composed of 10 or less sugars.

For example, the compound other than agarobiose and κ-carabiose having 3,6-anhydrogalactose at its reducing end used in the present invention is, without limitation, one in which a sugar is bound to a hydroxide group other than that at the 1-position of 3,6-anhydrogalactose. Examples thereof include products obtained by decomposition with acid, or digestion with α-agarase, of agarose such as agarobiose, agarotetraose, agarohexaose, agarooctaose and agarodecaose. Furthermore, products obtained by decomposition with acid, or digestion with carrageenase, of carrageenan can also be exemplified. Furthermore, the compounds other than agarobiose and κ-carabiose having 3,6-anhydrogalactose at their reducing ends used in the present invention include those in which one or more selected from the following is bound to a hydroxy group other than that at the 1-position of 3,6-anhydrogalactose: a hexose such as glucose, mannose and galactose; a pentose such as xylose, arabinose and ribose; a uronic acid such as glucuronic acid, a galacturonic acid, mannuronic acid and gluronic acid; an amino sugar such as glucosamine and galactosamine; a sialic acid such as N-acetylneuraminic acid; a deoxy sugar such as fucose; as well as esters, amides and/or lactones thereof. Furthermore, the following is also defined as the compound other than agarobiose and κ-carabiose having 3,6-anhydrogalactose at its reducing end used in the present invention: those in which a pyruvate group and/or a sulfate group is bound to agarobiose, κ-carabiose or the compound other than agarobiose and κ-carabiose having 3,6-anhydrogalactose at its reducing end, as well ones whose hydroxy group are methylated.

Since the carbon at the 1-position of 3,6-anhydrogalactose at the reducing end is an anomer carbon, an α-isomer and a β-isomer exist for a compound having 3,6-anhydrogalactose at its reducing end. Either can be used in the present invention as the compound having 3,6-anhydrogalactose at its reducing end. Furthermore, one having aldehyde at the 1-position of 3,6-anhydrogalactose at the reducing end can also be used as a compound having 3,6-anhydrogalactose at its reducing end. Either a D-isomer or an L-isomer of 3,6-anhydrogalactose may be used. In addition, a mixture of the α-isomer, the β-isomer and the aldehyde, as well as a mixture of the D-isomer and the L-isomer can also be used.

An apoptosis-inducing substance of the present invention can be obtained by treating a compound having 3,6-anhydrogalactose at its reducing end (e.g., a compound other than agarobiose and κ-carabiose having agarobiose, κ-carabiose or 3,6-anhydrogalactose at its reducing end) under neutral to alkaline conditions. It can also be obtained by acid decomposition at pH below 7 and/or enzymatic digestion of a 3,6-anhydrogalactose-containing material, followed by treatment of the product of the acid decomposition and/or the enzymatic digestion under neutral to alkaline conditions.

Any alkali can used to dissolve or suspend at least one compound selected from compounds having 3,6-anhydrogalactose at their reducing ends such as compounds other than agarobiose and κ-carabiose having agarobiose, κ-carabiose or 3,6-anhydrogalactose at their reducing ends in the treatment of the compound under alkaline conditions above pH 7. Inorganic bases such as sodium hydroxide, potassium hydroxide, calcium hydroxide and ammonium as well as organic bases such as tris, ethylamine and triethylamine can be used. The alkali can be used at a concentration of, without limitation, 0.0001 to 5 N, preferably 0.001 to 1 N. In addition, the reaction may be carried out, without limitation, at a temperature of 0 to 200° C., preferably 20 to 130° C. Furthermore, the reaction may be carried out, without limitation, for a few seconds to a few days. The alkali and the concentration thereof, and the temperature and time of the reaction may be suitable selected. Such selection depends on the following: the compound used as the raw material; and the yield of the apoptosis-inducing substance of interest. In general, the production of the apoptosis-inducing substance of the present invention proceeds more rapidly by selecting a high alkali concentration rather than a low alkali concentration (although any pH above 7 may be used), and a high temperature rather than a low temperature.

For example, the apoptosis-inducing substance of the present invention is produced by preparing a solution of agarobiose or κ-carabiose at pH 11.5 and incubating it at 37° C. for five minutes.

The alkaline solution that contains the thus produced apoptosis-inducing substance of the present invention may be used after being neutralized or as an acidic solution at pH below 7 depending on the purpose.

The apoptosis-inducing activity of the apoptosis-inducing substance of the present invention can be measured, for example, by using an antiproliferation activity against tumor cells as an index. The apoptosis-inducing substance of the present invention can be purified by using the activity as an index. Known means for purification including chemical and physical means can be used. The substance can be purified using purification means such as gel filtration, fractionation using a molecular weight fractionating membrane, solvent extraction and various chromatographies using ion exchange resins or the like in combination.

The apoptosis-inducing substance of the present invention in a purified form is exemplified by the compound of formula (I) as described above.

For example, a compound of formula (I) wherein X is CH$_2$OH and Y is H is purified from a product obtained by treating agarobiose under neutral to alkaline conditions. On the other hand, a compound of formula (I) wherein X is H and Y is CH$_2$OH is purified from a product obtained by treating κ-carabiose under neutral to alkaline conditions.

The compound of formula (I) used in the present invention is produced by treating 3,6-anhydrogalactose or a compound having 3,6-anhydrogalactose at its reducing end (e.g., a compound other than agarobiose and κ-carabiose having agarobiose, κ-carabiose or 3,6-anhydrogalactose at its reducing end) under neutral to alkaline conditions as described above. The present invention encompasses the compound of formula (I) used in the present invention as well as the use of 3,6-anhydrogalactose and/or the compound having 3,6-anhydrogalactose at its reducing end aiming at the exertion of its physiological activity.

The present invention encompasses the use of a prodrug aiming at the exertion of the activity of the compound of formula (I) of the present invention in vivo. 3,6-anhydrogalactose having a ligand that has an affinity with an organ or a tissue is preferably used as a prodrug. Such a prodrug is converted into a compound of formula (I) under physiological conditions after being incorporated into cells, and exerts various physiological functions. Galactose is exemplified as a ligand. Efficient targeting to liver tissues, among others, is accomplished by using galactose as a ligand. Compounds having such a ligand include agarooligosaccharides such as agarobiose, agarohexaose and agarooctaose having galactose at its non-reducing end. The agarooligosaccharides are useful as prodrugs.

Humans have taken agarooligosaccharides having galactose at their non-reducing ends for a long time. The agarooligosaccharide exerts its physiological activity after the 3,6-anhydrogalactose at the reducing end is freed under neutral or alkaline conditions and converted into a compound of formula (I). That is, an agarooligosaccharide absorbed into a living body as a prodrug is converted into a compound of formula (I) to exert its physiological activity. The agarooligosaccharides have an appropriate molecular weight for its efficient absorption. Therefore, they are readily absorbed at a digestive tract. Furthermore, the galactose at the non-reducing end makes the agarooligosaccharide be actively absorbed at a liver and facilitates its circulation in a bloodstream through the liver. After being absorbed, the agarooligosaccharide is converted into a compound of formula (I) at a local site in a tissue that has an affinity for the galactose at the non-reducing end to exert its physiological activity. Thus, an agarooligosaccharide can be administered as a prodrug, which is highly stable, efficiently incorporated, and converted into a compound of formula (I) at a local site in a concentrated state, to exert its physiological activity.

The salts of the compounds of formula (I) include pharmaceutically acceptable salts. Known methods can be used to convert the compounds into the salts.

The compound of formula (II) used in the present invention is generated in a reaction mixture obtained by reacting a compound of formula (I) with an SH group-containing compound.

Examples of the SH group-containing compounds to be used include, but are not limited to, methanethiol, butanethiol, mercaptoethanol, SH group-containing amino acids and SH group-containing amino acid derivatives. Examples of the SH group-containing amino acids include cysteine and homocysteine.

Examples of the SH group-containing amino acid derivatives include the derivatives of the above-mentioned amino acids such as cysteine derivatives, cysteine-containing peptides and cysteine derivative-containing peptides. The cysteine-containing peptide is not limited to specific one as long as the peptide has cysteine as its constituent. The cysteine-containing peptides of the present invention include small molecules such as oligopeptides (e.g., glutathione) and macromolecules such as proteins. Furthermore, peptides that contain cystine or homocystine can be used as cysteine- or homocysteine-containing peptides in the present invention by incorporating a treatment under conditions that generate cysteine- or homocysteine-containing peptides during the reaction, for example, under reductive conditions. The cysteine-containing peptides also include cysteine-containing peptides that contain a saccharide, a lipid or the like. Alternatively, the salts, acid anhydrides, esters or the like of the various substances as described above may be used.

The reaction between a compound of formula (I) and an SH group-containing compound for producing a compound of formula (II) may be conducted under known reaction conditions. The reaction may be conducted under any conditions in which the SH group of the SH group-containing compound is reactive.

Known means for purification including chemical and physical means can be used for purifying and isolating a compound of formula (II) generated by reacting a compound of formula (I) with an SH group-containing compound or a derivative thereof.

The compound of formula (I) reacts with, for example, an SH group-containing compound such as cysteine and glutathione in vivo to produce a metabolic derivative represented by formula (II), which is useful as a pharmaceutical. Thus, the drug efficacy exerted by the metabolic derivative can also be obtained by administering a compound of formula (I). Therefore, the present invention encompasses the use of a compound of formula (I) aiming at the generation of a compound of formula (II) in vivo.

The salts of the compounds of formula (II) include pharmaceutically acceptable salts. Known methods can be used to convert the compounds into the salts.

The compounds of formula (I), the compounds of formula (II) as well as the salts thereof used in the present invention have physiological activities such as an apoptosis-inducing activity, a carcinostatic activity, antioxidant activities such as an activity of inhibiting active oxygen production, an activity of inhibiting lipid peroxide radical production and an activity of inhibiting nitrogen monoxide production, an antimicrobial activity to pathogenic microorganism, an antimutagenic activity, an activity of inhibiting α-glycosidase, an immunoregulatory activity, an activity inhibiting prostaglandin synthesis, an anti-inflammatory activity, an anti-allergic activity, an activity of regulating cytokine production, an antirheumatic activity, an antidiabetic activity, an activity of inhibiting synovial cell proliferation, and an activity of inducing heat shock protein production. Based on these activities, pharmaceutical compositions for treating or preventing the following diseases can be produced using a compound selected from the group consisting of the compounds of formula (I), the compounds of formula (II) and salts thereof as an active ingredient. Such diseases include a disease that requires induction of apoptosis for its treatment or prevention, a cancerous disease, a disease that requires inhibition of active oxygen production for its treatment or prevention, a disease that requires inhibition of lipid peroxide radical production for its treatment or prevention, a disease that requires inhibition of nitrogen monoxide production for its treatment or prevention, a disease caused by a pathogenic microorganism, a disease induced by a mutagen, a disease that requires inhibition of α-glycosidase for its treatment or prevention, a disease that requires immunoregulation for its treatment or prevention, a disease that requires inhibition of prostaglandin synthesis for its treatment or prevention, a disease that requires inhibition of inflammation for its treatment or prevention, a disease that requires inhibition of allergy for its treatment or prevention, a disease that requires regulation of cytokine production for its treatment or prevention, rheumatism, diabetes, a disease that requires inhibition of synovial cell proliferation for its treatment or prevention, and a disease that requires induction of heat shock protein production for its treatment or prevention. In other words, the following pharmaceutical compositions can be produced: a composition for inducing apoptosis, a carcinostatic composition, antioxidant compositions such as a composition for inhibiting active oxygen production, a composition for inhibiting lipid peroxide radical production and a composition for inhibiting nitrogen monoxide production, an antimicrobial composition, an antiviral composition, an antimutagenic composition, an anti-hyperglycemic composition, an anti-hyperlipidemic composition, an immunoregulatory composition, a composition for inhibiting prostaglandin synthesis, an anti-inflammatory composition, an antiallergic composition, a composition for regulating cytokine production, a composition for inhibiting synovial cell proliferation, an antirheumatic composition, an antidiabetic composition, and a composition for inducing heat shock protein production.

The composition for inducing apoptosis of the present invention, which contains a compound selected from the group consisting of the compounds of formula (I), the compounds of formula (II) and salts thereof as an active ingredient, is useful for eliminating auto-reactive lymphocytes from patients with autoimmune diseases, tumor cells, cells infected with a virus and the like. It can be used to eliminate unnecessary or harmful cells from a living body in a natural manner by inducing apoptosis in desired tissues or cells. Examples of diseases for which the composition for inducing apoptosis of the present invention is effective include autoimmune diseases such as systemic lupus erythematosus, immune-mediated glomerulonephritis, multiple sclerosis and collagen disease, and rheumatism.

The composition for inducing apoptosis of the present invention can be used in a method for inducing apoptosis. The method is useful for elucidating the mechanism of induction of apoptosis, as well as screening for inducers of apoptosis and inhibitors of apoptosis induction.

The apoptosis-inducing activity of the composition for inducing apoptosis of the present invention is inhibited by a caspase inhibitor such as IL-1β converting enzyme inhibitor V [Z-Val-Ala-DL-Asp(OMe)-fluoromethylketone: Takara Shuzo]. Thus, the apoptosis induced by the composition is considered to be a cell death due to apoptosis that depends on caspase.

Caspase has been demonstrated to function as an important mediator of apoptosis for the following reasons: it is increases prior to various cell death; its overexpression induces cell death; the apoptosis is inhibited by a peptide inhibitor or an inhibitory protein such as CrmA and p35; and the apoptosis is partially inhibited in a knockout mouse for caspase-1 or caspase-3 as compared with a normal one [Seikagaku (Biochemistry), 70:14–21 (1998)]. That is, a cysteine protease, caspase, is activated during apoptotic process to degrade nuclear or cytoplasmic proteins. Caspase is first synthesized as a precursor and then activated by processing. The regulation of the caspase activation pathway decides the fate of cells. The mammals have ten or more types of caspases. Upstream caspases process downstream caspases to amplify the intracellular proteolytic activities in a cascade mode [Saibo Kogaku (Cell Technology), 17:875–880 (1998)]. On the contrary, inhibition of the processing activity using an inhibitor of the cysteine protease, caspase, can cease the cell death due to the caspase-dependent apoptosis.

The compounds of formula (I), the compounds of formula (II) and salts thereof used in the present invention are useful for inhibition of production of oxidizing substances such as active oxygen. Therefore, an antioxidant composition such as a composition for inhibiting active oxygen production that contains the compound as its active ingredient is useful for treating or preventing diseases caused by production and/or excess of active oxygen.

Active oxygen can be generally classified into radical active oxygen and non-radical active oxygen. The radical active oxygen includes hydroxy radical, hydroxyperoxy radical, peroxy radical, alkoxy radical, nitrogen dioxide, nitric monoxide (hereinafter referred to as NO), thylradical and superoxide. On the other hand, the non-radical active oxygen includes singlet oxygen, hydrogen peroxide, lipid hydroperoxide, hypochlorous acid, ozone and peroxonitrite. All of them are involved in a number of pathological states such as various inflammatory diseases, diabetes, cancers, arteriosclerosis, neurological diseases and ischemic re-perfusion disorder.

Active oxygen is always produced at a low concentration through several pathways in a living body. The thus produced active oxygen is inevitable and includes the following: superoxide and hydrogen peroxide physiologically leaking out from an electron transport system such as that in mitochondria, hydroxy radical whose production is catalyzed by a transition metal such as or monocytes for defense against infections and NO produced by decomposition of arginine. A living body has a system for eliminating active oxygen including enzymes and small molecule compounds against the production of the active oxygen to maintain the balance between the production and the elimination. However, the living body is oxidatively damaged if the production system becomes predominant over the elimination system due to the activation of the production system for some reasons or, to the contrary, due to the inactivation of the elimination system. Such conditions are called as oxidative stress. Furthermore, in addition to the internal imbalance, the living body is always exposed to oxidative stress due to external materials such as atmosphere and foods. Therefore, the oxidative stress is inevitable in everyone's daily life.

In other words, a living body is always exposed to circumstances which lead to the diseases caused by or worsening of the disease conditions due to oxidative stress, which is involved in various diseases as described above. Therefore, the antioxidant composition such as the composition for inhibiting active oxygen production of the present invention is also useful for preventing and treating the diseases caused by the oxidative stress or preventing the worsening of the disease conditions due to the oxidative stress.

A lipid peroxidation reaction is always associated with the oxidative stress. The reaction proceeds once a lipid peroxide radical is produced. 4-hydroxy-2-nonenal (HNE) produced in the reaction is a toxic aldehyde that specifically targets glutathione or proteins. The products of the reaction between HNE and proteins are detected in various disease tissues and considered to be inducers of disease conditions associated with oxidative stress. Accordingly, the antioxidant composition containing the antioxidant substance used in the present invention (i.e., a compound selected from the group consisting of the compounds of formula (I), the compounds of formula (II) and salts thereof), which can inhibit production of lipid peroxide radicals, as an active ingredient is useful for preventing and treating age-related diseases caused by oxidative stress.

NO is the essential component of endothelium-derived relaxing factor (EDRF) [Nature, 327:524–526 (1987)]. The present invention provides a pharmaceutical composition for treating or preventing a disease that requires inhibition of NO production for its treatment or prevention.

Examples of diseases that require inhibition of NO production for their treatment or prevention according to the present invention include, but are not limited to, systemic hypotension caused by toxic shock, treatment with certain cytokines and the like, reduction in blood pressure response, diabetes, vascular dysfunction, angiectasis caused by diseases, tissue injury, cardiovascular ischemia, hyperalgesia, cerebral ischemia, diseases accompanying vascularization, cancers and the like.

Nitric oxide synthases (NOS) produces L-citrulline and NO from L-arginine and oxygen. A cNOS which is constitutively expressed and an iNOS which is inducible are known for the NOSs. iNOS is induced by stimulation with cytotoxin or cytokines such as LPS and IFN-γ to produce NO in macrophages and the like. iNOS itself is essential to maintain the system of an organism. On the other hand, it has been demonstrated that iNOS causes various diseases when it is over-expressed due to various factors and produces excess NO.

The present inventors have confirmed that the compound of formula (I), the compound of formula (II) and salts thereof inhibit the expression of iNOS. The confirmation was carried out at protein level by using Western blotting and at messenger RNA level by using RT-PCR. Thus, a compound selected from the group consisting of the compounds of formula (I), the compounds of formula (II) and salts thereof used in the present invention inhibits the expression of iNOS, which is overexpressed due to various factors, resulting in the production of excess NO. Therefore, the compound is effective in treating and preventing diseases that require inhibition of NO production for their treatment and prevention.

The compound of formula (I), the compound of formula (II) and salts thereof used in the present invention inhibit NO production in macrophages. Thus, they are useful for treating and preventing diseases caused by NO production in macrophages, carcinogenesis and the like. The inhibition of No production by the compound used in the present invention does not antagonistically inhibit the inducers of NO production such as LPS or IFN-γ. The effect of inhibiting NO production is enhanced when the compound used in the present invention is added in advance. Therefore, the compound selected from the group consisting of the compounds of formula (I), the compounds of formula (II) and salts thereof used in the present invention is very useful as an active ingredient of a composition for preventing the production of antioxidant substances.

The composition for inhibiting NO production of the present invention is useful for studying the mechanism of NO production and the mode of action of NO and can be used for screening of substances that participate in the mechanism of No production.

Vascularization is necessary for the growth of a solid cancer. Vascular endothelial growth factor/vascular permeability factor (VEGF) plays important roles in this process. NO induces VEGF in various tumor cells. The composition for inhibiting NO production of the present invention also inhibits VEGF production in tumor cells by inhibiting NO production, thereby inhibiting vascularization around cancer tissues. When the composition for inhibiting NO production of the present invention is administered to a mouse in which tumor cells have been transplanted subcutaneously to form solid cancers, vascularization around the cancer tissue becomes insufficient and the cancer falls out.

Nitrosoamines are a series of compounds in which nitrso group is attached to a secondary amine. Many of the several hundred types of nitrosoamines known in the art exhibit carcinogenic activity on animals by damaging their DNA. Nitrosoamines are considered to have a profound relation to carcinogenesis in humans. Nitrosoamine is usually produced by a reaction between a nitrite and an amine in a stomach. NO produces a nitrosoamine by reaction with an amine even under physiological conditions at neutral pH. NO production is increased in patients with clonorchiasis or cirrhosis, which epidemiologically have high relationship with cancers. Therefore, carcinogenesis of a high-risk group, in particular, can be prevented by administrating the composition for inhibiting NO production of the present invention to prevent the increase in NO production. As described above, the composition for inhibiting NO production of the present invention exhibits its carcinostatic activity in two steps, that is, suppression of carcinogenesis and inhibition of vascularization in cancerous tissues.

The compound used in the present invention exerts its carcinostatic activity as a result of two synergistic effects. One is a direct effect of inducing apoptosis to kill tumor cells. Another is an indirect effect of forcing tumor cells to die by inhibiting vascularization involving VEGF induced by NO, which is accomplished by inhibiting NO production in the tumor cells.

NO also induces edema, which is characteristically observed in inflammatory lesion. In other words, it increases vascular permeability [Maeda et al., Japanese Journal of Cancer Research, 85:331–334 (1994)]. No increases biosynthesis of prostaglandins which are inflammatory mediators [Salvemini et al., Proceedings of National Academy of Sciences, USA, 90:7240–7244 (1993)]. On the other hand, NO rapidly reacts with superoxide radical to produce peroxonitrite ion. This peroxonitrite ion is considered to cause inflammatory damages of cells and tissues.

NO production is induced when activated immune cells enter into an organ and release cytokines. Insulin-dependent diabetes is caused by specific destruction of islet β cells, which destruction is considered to be caused by NO. Synovial fluid in the lesion of a patient with rheumatoid arthritis, osteoarthrosis, gouty arthritis or arthritis associated with Behcet's disease contains NO at a concentration higher than that in the normal joint of the same patient or joints of a healthy individual. When the composition for inhibiting NO production of the present invention is administered to such a patient, NO production in the lesion is inhibited, resulting in the improvement of disease conditions.

NO production is increased during cerebral ischemia and after re-perfusion, resulting in damages in cerebral tissues. Administration of the composition for inhibiting NO production of the present invention to a patient during cerebral ischemia relieves the damage in cerebral tissue and improves the prognosis.

Arachidonic acid metabolism is greatly involved in the rise of inflammation and dolor in tissues. Arachidonic acid derived from phospholipid in cell membrane is metabolized in vivo into prostaglandin, prostacyclin and thromboxane by the action of cyclooxygenase. Among these, prostaglandin has an angiectatic activity and, consequently, an activity of increasing bloodstream to organs. In particular, prostaglandins $E_2$ and $I_2$ increase edemas and leukocyte infiltration at inflammation sites due to their activity of increasing bloodstream. Thus, sedative and anti-inflammatory activities can be exerted by administering the composition for inhibiting prostaglandin $E_2$ synthesis of the present invention to inhibit the biosynthesis of prostaglandin. Furthermore, leukocytes infiltrated into inflammation site produce active oxygen and cause oxidative stress conditions. Accordingly, the composition for inhibiting prostaglandin $E_2$ synthesis of the present invention which inhibits the biosynthesis of prostaglandin is also useful for the prevention, treatment or prevention of worsening of various diseases caused by oxidative stress as described above.

In addition, NO induces edema which is characteristically observed in inflammatory lesions, i.e., increases vascular permeability, and increases biosynthesis of prostaglandins which are inflammatory mediators as described above. The effect of inhibiting NO production and the effect of inhibiting prostaglandin $E_2$ synthesis of the present invention act synergistically to exhibit sedative and anti-inflammatory activities as well as synergistic effects in the prevention, treatment or prevention of worsening of various diseases caused by oxidative stress. The immunoregulatory composition of the present invention has immunoregulatory activities such as an activity of inhibiting lymphocyte blastogenesis and an activity of inhibiting mixed lymphocyte reaction. Thus, the immunoregulatory composition of the present invention is useful as a pharmaceutical composition for treating or preventing diseases due to abnormality of the immune systems or immune factors.

Lymphocyte blastogenesis is a reaction in which mitogen binds to a receptor on the surface of a lymphocyte to activate the lymphocyte and promotes its division and proliferation. Mixed lymphocyte reaction is a reaction in which lymphocytes obtained from allogeneic animals are mixed and cultured, thereby inducing activation of lymphocytes due to incompatibility of major histocompatibility antigens to promote the division and proliferation of lymphocytes. The immunoregulatory composition of the present invention inhibits these reactions and is particularly useful for treating and preventing chronic diseases caused by abnormal increase in lymphocytes, for example, autoimmune diseases such as chronic nephritis, chronic colitis, type I diabetes and rheumatoid arthritis and is also useful for suppression of graft rejection.

The compound of formula (I), the compound of formula (II) and salts thereof have an activity of inducing the production of heat shock proteins such as 70-kDa heat shock protein (HSP70). They have antiviral activities against RNA viruses and DNA viruses such as hepatitis virus, AIDS virus, influenza virus, vesicular stomatitis virus and herpesvirus. Heat shock proteins are involved in tumor immunity. Thus, these compounds are also effective for tumor immunity. In addition, heat shock proteins are involved in biological defense including anti-inflammation. Thus, viral diseases such as a cold due to influenza virus can be prevented or treated by administering the compound of formula (I), the compound of formula (II) and salts thereof.

The composition for inducing apoptosis of the present invention can be prepared by using a compound selected from the group consisting of the compound of formula (I), the compound of formula (II) and salts thereof as its active ingredient, and formulating it with a known pharmaceutical carrier. The composition is generally mixed with a pharmaceutically acceptable liquid or solid carrier and, optionally, solvent, dispersing agent, emulsifier, buffering agent, stabilizer, excipient, binder, disintegrant, lubricant and the like to formulate it. The formulation may be in a form of a solid preparation such as tablet, granule, powder, epipastic and capsule, or a liquid preparation such as normal solution, suspension and emulsion. In addition, the composition may be formulated into a dried preparation, which can be reconstituted as a liquid preparation by adding an appropriate carrier before use.

The composition for inducing apoptosis of the present invention can be administered as either an oral preparation or a parenteral preparation such as injectable preparation and drips.

The pharmaceutical carrier can be selected according to the above-mentioned particular administration route and dosage form. For an oral preparation, starch, lactose, sucrose, mannit, carboxymethylcellulose, cornstarch, inorganic salts and the like are utilized, for example. Binder, disintegrant, surfactant, lubricant, fluidity-promoting agent, tasting agent, coloring agent, flavoring agent and the like can also be included in oral preparations.

A parenteral preparation can be prepared according to conventional methods by dissolving or suspending the active ingredient of the present invention, i.e., a compound selected from the group consisting of the compound of formula (I), the compound of formula (II) and salts thereof, in a diluent. The diluents include injectable distilled water, physiological saline, aqueous glucose solution, injectable vegetable oil, sesame oil, peanut oil, soybean oil, corn oil, propylene glycol and polyethylene glycol. Optionally, sterilizer, stabilizer, osmotic regulator, smoothing agent and the like may be added to the solution or suspension.

The composition for inducing apoptosis of the present invention is administered through a suitable route for the dosage form of the composition. The administration route is not limited to a specific one. The composition can be administered internally or externally (or topically) or by injection. The injectable preparation can be administrated intravenously, intramuscularly, subcutaneously, intradermally and the like, for example. External preparations include a suppository.

A dosage of the composition for inducing apoptosis of the present invention is appropriately determined and varies depending on the particular dosage form, administration route and purpose as well as age, weight and conditions of a patient to be treated. In general, a daily dosage for an adult person is 10 $\mu$g to 200 mg/kg in terms of the amount of the active ingredient contained in the formulation. Of course, the dosage can vary depending on various factors. Therefore, in some cases, a less dosage than the above may be sufficient but, in other cases, a dosage more than the above may be required. The pharmaceutical composition of the present invention can be administered orally as it is, or it can be taken daily by adding to selected foods and drinks.

The carcinostatic composition of the present invention can be prepared by using a compound selected from the group consisting of the compound of formula (I), the compound of formula (II) and salts thereof as its active ingredient and formulating it with a known pharmaceutical carrier. The carcinostatic composition can be prepared according to the same manner as that described above with respect to the composition for inducing apoptosis.

The carcinostatic composition is administered through a suitable route for the dosage form of the composition. The administration route is not limited to a specific one. The composition can be administrated internally or externally (or topically) or by injection. An injectable preparation can be administrated, for example, intravenously, intramuscularly, subcutaneously, intradermally and the like. External preparations include a suppository.

A dosage of the carcinostatic composition is appropriately determined and varies depending on the particular dosage form, administration route and purpose as well as age, weight and conditions of a patient to be treated. In general, a daily dosage for an adult person is 10 $\mu$g to 200 mg/kg in terms of the amount of the active ingredient contained in the formulation. Of course, the dosage can vary depending on various factors. Therefore, in some cases, a less dosage than the above may be sufficient, but, in other cases, a dosage more than the above may be required. The pharmaceutical composition of the present invention can be administrated orally as it is, or it can be taken daily by adding to selected foods and drinks.

Rheumatism is an autoimmune disease in which periosteal cells and chondrocytes are damaged. The compound of formula (I), the compound of formula (II) and salts thereof have an apoptosis-inducing activity on synovial cells. Thus, an antirheumatic composition can be prepared by using a compound selected from the group consisting of the compound of formula (I), the compound of formula (II) and salts thereof as its active ingredient and formulating it with a known pharmaceutical carrier. The antirheumatic composition can be prepared according to the same manner as that described above.

The antirheumatic composition can be administered as either an oral preparation or a parenteral preparation such as injectable preparation and drips.

The pharmaceutical carrier can be selected according to the above-mentioned particular administration route and dosage form and may be used according to the same manner as that described above with respect to the composition for inducing apoptosis.

The antirheumatic composition is administered through a suitable route for the dosage form of the composition. The administration route is not limited to a specific one. The composition can be administrated internally or externally (or topically) or by injection. An injectable preparation can be administrated, for example, intravenously, intramuscularly, subcutaneously, intradermally and the like. External preparations include a suppository.

A dosage of the antirheumatic composition that contains a compound selected from the group consisting of the compound of formula (I), the compound of formula (II) and salts thereof as its active ingredient is appropriately determined and varies depending on the particular dosage form, administration route and purpose as well as age, weight and conditions of a patient to be treated. In general, a daily dosage for an adult person is 0.01 to 50 mg, preferably 0.1 to 10 mg in terms of the amount of the active ingredient contained in the formulation. Of course, the dosage can vary depending on various factors. Therefore, in some cases, a less dosage than the above may be sufficient, but, in other cases, a dosage more than the above may be required. The pharmaceutical composition of the present invention can be administrated orally as it is, or it can be taken daily by adding to selected foods and drinks.

Additionally, the following compositions can be prepared by using a compound selected from the group consisting of the compound of formula (I), the compound of formula (II) and salts thereof as its active ingredient according to the same manner as that described above with is respect to the composition for inducing apoptosis: an antioxidant composition, a composition for inhibiting active oxygen production, a composition for inhibiting lipid peroxide radical production, a composition for inhibiting NO production, an antimicrobial composition to pathogenic microorganism, an antimutagenic composition, a composition for inhibiting prostaglandin synthesis, a composition for inhibiting synovial cell proliferation, a composition for inducing heat shock protein production and an antiviral composition. The same dosage and administration route as those described above with respect to the composition for inducing apoptosis can be used depending on the conditions.

The compound of formula (I), the compound of formula (II) and salts thereof exhibit inhibitory activities against various α-glycosidases such as sucrase and maltase. Therefore, an anti-hyperglycemic composition, an anti-hyperlipidemic composition, an anti-obese composition, an antidiabetic composition and the like can be prepared using the compound of formula (I) as its active ingredient. Such pharmaceutical compositions can be prepared according to the same manner as that described above with respect to the composition for inducing apoptosis. The same dosage and administration route as those described above with respect to the composition for inducing apoptosis can be used depending on the conditions. A composition for inhibiting α-glycosidase can be prepared using a compound selected from the group consisting of the compound of formula (I), the compound of formula (II) and salts thereof as its active ingredient according to a conventional method. A method for inhibiting α-glycosidase can be carried out using the composition for inhibiting α-glycosidase.

The present invention provides foods or drinks containing, produced by diluting and/or produced by adding thereto a compound selected from the group consisting of the compound of formula (I), the compound of formula (II) and salts thereof. The food or drink of the present invention has an apoptosis-inducing activity, a carcinostatic activity, an antioxidant activity, an antimicrobial activity to pathogenic microorganism, an antimutagenic activity, an activity of inhibiting prostaglandin synthesis, an activity of inducing heat shock protein production, an antiviral activity, an activity of inhibiting α-glycosidase and the like. Thus, it is very useful for ameliorating disease states of and preventing diseases sensitive to a compound selected from the group consisting of the compound of formula (I), the compound of formula (II) and salts thereof, such as a disease that requires induction of apoptosis for its treatment or prevention, a cancerous disease, a disease that requires inhibition of active oxygen production for its treatment or prevention, a disease that requires inhibition of NO production for its treatment or prevention, a disease caused by a pathogenic microorganism, a disease that is raised by a mutagen, prostaglandin synthesis or the like, a disease that requires induction of heat shock protein production for its treatment or prevention, a viral disease, a disease that requires regulation of α-glycosidase for its treatment or prevention and the like.

The process for producing the foods or drinks of the present invention is not limited to a specific one. Any processes including cooking, processing and other generally employed processes for producing foods and drinks can be used as long as the resultant foods or drinks contain, are produced by adding thereto and/or are produced by diluting a compound selected from the group consisting of the compound of formula (I), the compound of formula (II) and salts thereof as their active ingredients.

For example, in the production of the foods or drinks, the compound of formula (I) is obtained by treating 3,6-anhydrogalactose and/or a compound having 3,6-anhydrogalactose at its reducing end under neutral to alkaline conditions. 3,6-anhydrogalactose and/or a compound having 3,6-anhydrogalactose at its reducing end is obtained by hydrolysis under acidic conditions or enzymatic digestion of a 3,6-anhydrogalactose-containing material.

For example, agar, agarose and/or carrageenan can be used as a 3,6-anhydrogalactose-containing material. At least one compound selected from the group consisting of agarobiose, κ-carabiose and a compound other than agarobiose and κ-carabiose having 3,6-anhydrogalactose at its reducing end can be used as a compound having 3,6-anhydrogalactose at its reducing end.

The foods or drinks of the present invention also include foods or drinks containing, produced by diluting and/or produced by adding thereto the compound of formula (II) generated by the reaction between the compound of formula (I) and an SH group-containing compound during the production of the foods or drinks The foods or drinks of the present invention are not limited to a specific one and examples thereof include the following: products of processed cereal (e.g., wheat flour product, starch product, premixed product, noodle, macaroni, bread, bean jam, buckwheat noodle, wheat-gluten bread, rice noodle, gelatin noodle and packed rice cake), products of processed fat and oil (e.g., plastic fat and oil, tempura oil, salad oil, mayonnaise and dressing), products of processed soybeans (e.g., tofu, miso and fermented soybean), products of processed meat (e.g., ham, bacon, pressed ham and sausage), processed marine products (e.g., frozen ground fish, boiled fish paste, tubular roll of boiled fish paste, cake of ground fish, deep-fried patty of fish paste, fish ball, sinew, fish meat ham or sausage, dried bonito, product of processed fish egg, canned marine product and fish boiled in sweetened soy sauce), dairy products (e.g., raw milk, cream, yogurt, butter, cheese, condensed milk, powdered milk and ice cream), products of processed vegetables and fruits (e.g., paste, jam, pickle, fruit juice, vegetable drink and mixed drink), confectioneries (e.g., chocolate, biscuit, sweet bun, cake, rice-cake sweet and rice sweet), alcohol drinks (e.g., sake, Chinese liquor, wine, whisky, shochu, vodka, brandy, gin, rum, beer, soft alcohol drink, fruit liquor and liqueur), luxury drinks (e.g., green tea, tea, oolong tea, coffee, soft drink and lactic acid drink), seasonings (e.g., soy sauce, sauce, vinegar and sweet sake), canned, bottled or bagged foods (e.g., various cooked foods such as rice topped with cooked beef and vegetables, rice boiled together with meat and vegetables in a small pot, steamed rice with red beans, and curry), semi-dried or condensed foods (e.g., liver paste, other spreads, soup for buckwheat noodle or udon and condensed soup), dried foods (e.g., instant noodle, instant curry, instant coffee, powdered juice, powdered soup, instant miso soup, cooked food, cooked drink and cooked soup), frozen foods (e.g., sukiyaki, chawan-mushi, grilled eel, hamburger steak, shao-mai, dumpling stuffed with minced pork, various stick-shaped foods and fruit cocktail), solid or liquid foods (e.g., soup), processed agricultural or forest products (e.g., spice), processed livestock products, processed marine products and the like.

In so far as the foods or drinks of the present invention contain, are produced by diluting and/or are produced by adding thereto a compound selected from the group consisting of the compound of formula (I), the compound of formula (II) and salts thereof in an amount necessary for exhibiting its physiological function, their forms are not limited to a specific one The foods or drinks may be in any edible forms such as tablets, granules and capsules.

The foods or drinks of the present invention contain a compound selected from the group consisting of the compound of formula (I), the compound of formula (II) and salts thereof, which has a physiological activity. The physiological functions of the compound such as an apoptosis-inducing activity and a carcinostatic activity provide an effect of preventing carcinogenesis, an effect of suppressing cancers or the like upon taking the foods or drinks. That is, the foods or drinks of the present invention are healthy foods or drinks which have effects of ameliorating the disease states of or preventing the diseases sensitive to the compound of formula (I), the compound of formula (II) and salts thereof. Particularly, they are useful for keeping gastrointestinal health.

Additionally, the foods or drinks containing, produced by diluting and/or produced by adding thereto a compound selected from the group consisting of the compound of formula (I), the compound of formula (II) and salts thereof are useful as anti-hyperglycemic, antidiabetic, anti-obese or anti-hyperlipidemic foods or drinks based on the activity of inhibiting α-glycosidase of the compound.

Furthermore, the compound of formula (I), the compound of formula (II) and salts thereof have antioxidant activities such as an activity of inhibiting active oxygen production and an activity of inhibiting lipid peroxide radical production. Therefore, they can be used in the production of antioxidant foods or drinks as antioxidant compositions for antioxidant foods or drinks such as a composition for inhibiting active oxygen production, a composition for inhibiting lipid peroxide radical production and a composition for inhibiting NO production.

The formulation of the antioxidant composition of the present invention containing at least one compound selected from the above-mentioned compounds as an active ingredient is not limited to a specific one. The composition can be suitably formulated into, for example, powders, pastes, emulsions and the like depending on the foods and drinks into which the compound is applied according to conventional methods. The foods or drinks that contain the compounds used in the present invention as their active ingredient can be conveniently produced by using the antioxidant composition of the present invention.

The present invention provides a compound for antioxidation represented by formula (I) or formula (II).

For example, the compound for antioxidation represented by formula (I) can be obtained by treating under neutral to alkaline conditions a product produced by acid decomposition under acidic conditions below pH 7 and/or enzymatic digestion of a 3,6-anhydrogalactose-containing material. Both of the purified and partially purified materials can be used.

Examples of the 3,6-anhydrogalactose-containing materials which can be used include those derived from red algae such as agar, agarose and/or carrageenan.

The compound for antioxidation represented by formula (II) can be obtained by reacting the compound of formula (I) and an SH group-containing compound. Both of the purified and partially purified materials can be used.

The compound for antioxidation of the present invention is useful for eliminating or suppressing the production of oxidants in a living body, such as active oxygen. Thus, the compound is useful for ameliorating disease states of or preventing diseases caused by production and/or excess of active oxygen.

As described above, oxidative stress, which is generated by oxidatively damaging a living body when the system for producing active oxygen becomes predominant over the elimination system in the living body, is involved in various diseases. Thus, a living body is always exposed to circumstances which lead to diseases caused by oxidative stress or worsening of the diseases conditions. Therefore, it is desirable to take a suitable amount of an antioxidant substance everyday for preventing, treating or preventing worsening of diseases caused by oxidative stress. For daily intake of suitable amount of an antioxidant substance, it is desirable to take it from foods and/or drinks. The foods and drinks which contain, produced by diluting, and/or produced by adding thereto the compound for antioxidation of the present invention are very useful as antioxidant foods or drinks or anti-oxidative stress foods or drinks.

The compound used in the present invention also has an ability of retaining water. Thus, it can be used as an active ingredient for the production of anti-constipation compositions, as well as anti-constipation foods or drinks.

The present invention further provides a cosmetic composition that contains a compound selected from the group consisting of the compound of formula (I), the compound of formula (II) and salts thereof as its active ingredient.

Cosmetic compositions containing the above-mentioned compound an active ingredient can be formulated into the following forms: fundamental cosmetic compositions such as cream, milky lotion, lotion, facial cleansing and pack, make-up cosmetics such as lipstick and foundation, body soap, soap and the like. The compound is also effective to the hair. The cosmetic composition of the present invention can be produced in the form of hair care products, for example, hair products such as hair tonic, hair liquid, hair set lotion, hair blow agent, hair cream and hair coat, as well as hair toiletry products such as shampoo, hair rinse and hair treatment. The amount of the compound mixed in the cosmetic composition can be determined appropriately depending on its whitening, moisturizing or antioxidant activity. As for the other components in the cosmetic composition, those mixed in conventional cosmetic compositions can be used. The whitening activity and the moisturizing activity can be measured by conventional methods such as those described in JP-A 8-310937.

The cosmetic composition of the present invention has excellent properties based on the whitening activity, the moisturizing activity, the antioxidant activity, the activity of inhibiting active oxygen production and the anti-oxidative stress activity on skin; as well as the moisturizing activity, the antioxidant activity, the activity of inhibiting active oxygen production and the anti-oxidative stress activity on hair; and the like.

The present invention provides a composition for preserving freshness which contains a compound selected from the group consisting of the compound of formula (I), the compound of formula (II) and salts thereof as its active ingredient. The compound of formula (I), the compound of formula (II) and salts thereof have an antioxidant activity, an activity of preserving freshness, an activity of inhibiting tyrosinase activity, anti-pathogenic microbial activity and an antimutagenic activity. Thus, a composition for preserving freshness of foods that effectively prevents color change, decay, oxidation and the like of foods can be produced according to a known formulation method by using a compound selected from the group consisting of the compound of formula (I), the compound of formula (II) and salts thereof as an active ingredient. The composition for preserving freshness of the present invention is very useful for keeping taste and freshness of various foods, perishables, processed foods and the like.

According to the present invention, a composition for inducing apoptosis can be produced using an apoptosis-inducing substance produced by treating 3,6-anhydrogalactose and/or a compound having 3,6-anhydrogalactose at its reducing end under neutral to alkaline conditions (hereinafter simply referred to as an apoptosis-inducing substance) as an active ingredient. Such composition may be prepared according to the same manner as that described above with respect to the composition for inducing apoptosis.

A dosage of the composition for inducing apoptosis containing the apoptosis-inducing substance of the present invention as its active ingredient is appropriately determined and varies depending on the particular dosage form, administration route and purpose as well as age, weight and conditions of a patient to be treated. In general, a daily dosage for an adult person is 10 μg to 200 mg/kg in terms of the amount of the active ingredient contained in the formulation. Of course, the dosage can vary depending on various factors. Therefore, in some cases, a less dosage than the above may be sufficient but, in other cases, a dosage more than the above may be required. The pharmaceutical composition of the present invention can be administrated orally as it is, or it can be taken daily by adding to selected foods and drinks.

The composition for inducing apoptosis containing the apoptosis-inducing substance of the present invention as its active ingredient has an antiproliferation activity against tumor cells. Thus, a carcinostatic composition can be produced using the apoptosis-inducing substance of the present invention as an active ingredient.

The same production method, dosage and administration route as those described above with respect to the composition for inducing apoptosis can be used for the carcinostatic composition containing the apoptosis-inducing substance of the present invention as its active ingredient.

The apoptosis-inducing substance of the present invention can be used as a pharmaceutical composition for treating a cancerous disease and the like. A method for inducing apoptosis using a compound represented by the apoptosis-inducing substance of the present invention as an active ingredient is useful for studying a mechanism of biological defense, cancerous diseases and the like as well as for developing inhibitors of apoptosis induction.

The foods and drinks which contain, which are produced by diluting, and/or which are produced by adding thereto the apoptosis-inducing substance of the present invention contain an effective amount of the substance for exerting its physiological activity. The process for producing the foods or drinks of the present invention (e.g., foods or drinks for inducing apoptosis or carcinostatic foods or drinks) is not limited to a specific one. Any processes including cooking, processing and other generally employed processes for producing foods and drinks can be used as long as the resultant foods or drinks contain an effective amount of the apoptosis-inducing substance of the present invention for exerting an apoptosis-inducing activity or a carcinostatic activity. The foods and drinks which contain, which are produced by diluting, and/or which are produced by adding thereto the apoptosis-inducing substance of the present invention generated by treating 3,6-anhydrogalactose and/or a raw material having 3,6-anhydrogalactose at its reducing end under alkaline conditions over pH 7 in the production of the foods or drinks are included in the foods or drinks of the present invention.

In so far as the foods or drinks of the present invention contain, are produced by adding thereto and/or are produced by diluting the apoptosis-inducing substance of the present invention, their forms are not limited to a specific one. The foods or drinks may be any edible forms such as tablets, granule and capsule.

The foods or drinks of the present invention have an apoptosis-inducing activity and a carcinostatic activity. Therefore, they are very useful for ameliorating disease states of or preventing cancers of digestive organs and the like.

No death was observed when either of the compound of formula (I), the compound of formula (II), salts thereof and the apoptosis-inducing substance of the present invention was orally administered to a mouse at a single dosage of 100 mg/kg.

As described above, the compound of formula (I), the compound of formula (II), salts thereof and the apoptosis-inducing substance of the present invention are very useful in a wide variety of fields including medicine, foods and drinks based on their various physiological functions.

The use of the compound of formula (I) and/or the apoptosis-inducing substance of the present invention artificially generated by treating 3,6-anhydrogalactose and/or a raw material having 3,6-anhydrogalactose at its reducing end under alkaline conditions over pH 7 in the production of foods or drinks is also encompassed by the present invention.

The use of the compound of formula (II) generated in foods or drinks or generated artificially as a product of reaction between the compound of formula (I) and an SH group-containing compound such as an SH group-containing amino acid or a derivative thereof such as cysteine or a cysteine-containing amino acid derivative (e.g., glutathione) is also encompassed by the present invention.

The following examples further illustrate the present invention in detail but are not to be construed to limit the scope thereof.

EXAMPLE 1

Preparation of L-glycero-1,5-epoxy-1αβ,6-dihydroxy-cis-hex-3-en-2-one (DGE) and D-glycero-1,5-epoxy-1αβ,6-dihydroxy-cis-hex-3-en-2-one (κ-DGE)

(1) 2.5 g of commercially available agar (Agar Noble, Difco) was suspended in 50 ml of 0.1 N HCl and the suspension was heated at 100° C. for 13 minutes to prepare a solution. After cooling to room temperature and adjusting the pH to about neutral pH with NaOH, the solution was filtered through a Cosmonice filter and separated on normal phase HPLC as follows.

Column: TSKgel Amide-80 (21.5 mm×300 mm, Toso)
Solvent A: 90% aqueous acetonitrile solution Solvent B: 50% aqueous acetonitrile solution Flow rate: 5 ml/min.

Elution: linear gradient from Solvent A to Solvent B (80 min.)→Solvent B (20 min.)

Detection: absorbance at 195 nm

Amount of sample applied: 2 ml

Peaks at retention time of 66.7, 78.5 or 85.5 minutes were collected and subjected to mass spectrometric analysis. It revealed that these substances were agarobiose, agarotetraose and agarohexaose, respectively.

The separation on HPLC as described above was repeated eight times. The fractions thus separated were evaporated to dryness under reduced pressure to obtain 122 mg of agarobiose, 111 mg of agarotetraose and 55 mg of agarohexaose, respectively.

(2) 12 µl of 1N NaOH was added to 600 µl of 100 mM aqueous solution of agarobiose obtained in Example 1-(1) (Sample 1) to adjust the pH to 11.5. The solution was incubated at 37° C. for 5 minutes. 12 µl of 1N HCl was then added to the solution to adjust the pH to about 5 (Sample 2). 1 µl of 1N HCl was further added to 50 µl of the solution to adjust the pH to about 2 (Sample 3).

The antiproliferation activities against tumor cells as apoptosis-inducing activities of the Samples 1 to 3 were measured as follows. As a result, each of the Samples had almost equivalent antiproliferation activities against tumor cells.

The Samples 1 to 3 were separately sterilized by filtration and appropriately diluted with sterile water. 10 µl of each dilution was placed in a well of a 96-well microtiter plate. 90 µl of RPMI 1640 medium (Nissui) containing 10% fetal bovine serum (Gibco), which had been treated at 56° C. for 30 minutes, and 5,000 HL-60 cells (ATCC CCL-240) was added thereto. The plate was incubated at 37° C. for 48 hours in the presence of 5% $CO_2$. The cell morphology was examined under an optical microscope. 10 µl of 5 mg/ml 3-(4,5-dimethylthiazol-2-yl)-2,5-diphenyltetrazolium bromide (Sigma) solution in phosphate buffered saline was further added thereto and the incubation was continued for additional 4 hours. 100 µl of 2-propanol containing 0.04 N HCl was added to the well and the mixture was thoroughly stirred. The absorbance at 590 nm was measured to determine the cell growth level.

(3) The Samples 1 to 3 as described in Example 1-(2) were spotted onto a silica gel sheet 60F254 (Merck) and developed using ethanol:1-butanol:water=5:5:1. Orcinol-sulfuric acid reagent was then sprayed to the sheet to detect spots. As a result, no spot for agarobiose was observed for the Sample 2 or the Sample 3 with several new spots observed.

10 µl each of the Samples 1 and 2 was separated on normal phase HPLC as follows.

Column: PALPAK Type S (4.6×250 mm, Takara Shuzo)

Mobile Phase A: 90% aqueous acetonitrile solution

B: 50% aqueous acetonitrile solution

Flow rate: 1 ml/min.

Elution: Mobile Phase A (10 min.)→linear gradient from Mobile Phase A to Mobile Phase B (40 min.)→Mobile Phase B (10 min.)

Detection: absorbance at 195 nm

Column temperature: 40° C.

As a result, the peak for agarobiose observed for the Sample 1 was not observed for the Sample 2, while plural new peaks were observed. The respective peaks of the Sample 2 were collected, evaporated to dryness under reduced pressure and dissolved in water. The antiproliferation activity against tumor cells was measured for each fraction in the same manner as that described above. As a result, the activity was present in the fraction at retention time of 4.05 to 4.16 minutes.

These results are shown in FIG. 1. FIG. 1 illustrates the normal phase HPLC chromatogram of the Sample 2. In FIG. 1, the horizontal axis represents the retention time (minutes) and the vertical axis represents the absorbance.

(4) Alkali-treated preparations were produced according to the method as described in Example 1-(2) from agarotetraose and agarohexaose prepared in Example 1-(1) as well as κ-carabiose prepared from decomposition product of κ-carrageenan with 0.1N hydrochloric acid. Their antiproliferation activities against tumor cells were then measured as described in Example 1-(2). As a result, antiproliferation activities against tumor cells were observed for each of the alkali-treated preparations.

κ-Carabiose was prepared as follows.

2.5 g of κ-carrageenan (Sigma, C-1263) was suspended in 50 ml of 0.1 N HCl and the suspension was heated at 100° C. for 16 minutes to prepare a solution. The solution was cooled to room temperature, neutralized to about neutral pH with NaOH, filtrated through a Cosmonice filter and separated on normal phase HPLC as described in Example 1-(3). The fraction containing κ-carabiose at elution time of 27.8 minutes was collected and evaporated to dryness under reduced pressure to prepare κ-carabiose.

(5) 2.5 g of commercially available agar (Agar Noble) was suspended in 50 ml of 0.1 N HCl and the suspension was heated at 100° C. for 13 minutes to prepare a solution. The solution was cooled to room temperature. The pH was adjusted to 12 with NaOH. The solution was then neutralized.

The neutralized solution was subjected to normal phase HPLC as described in Example 1-(3). The respective peaks were collected, evaporated to dryness under reduced pressure and dissolved in water. The antiproliferation activities against tumor cells of the respective fractions were measured as described above, confirming the antiproliferation activity of the fraction at retention time of 4.05 to 4.16 minutes. In addition, formation of apoptotic bodies was observed.

Next, the fraction at retention time of 4.05 to 4.16 minutes was collected in large quantities to prepare a sample for structure analysis.

Fast atom bombardment mass spectrometry (FAB-MS) was then carried out using DX302 mass spectrometer (Nippon Denshi). Furthermore, the sample was dissolved in heavy dimethyl sulfoxide and subjected to structure analysis by nuclear magnetic resonance (NMR). The results are shown below.

Figure 2A:
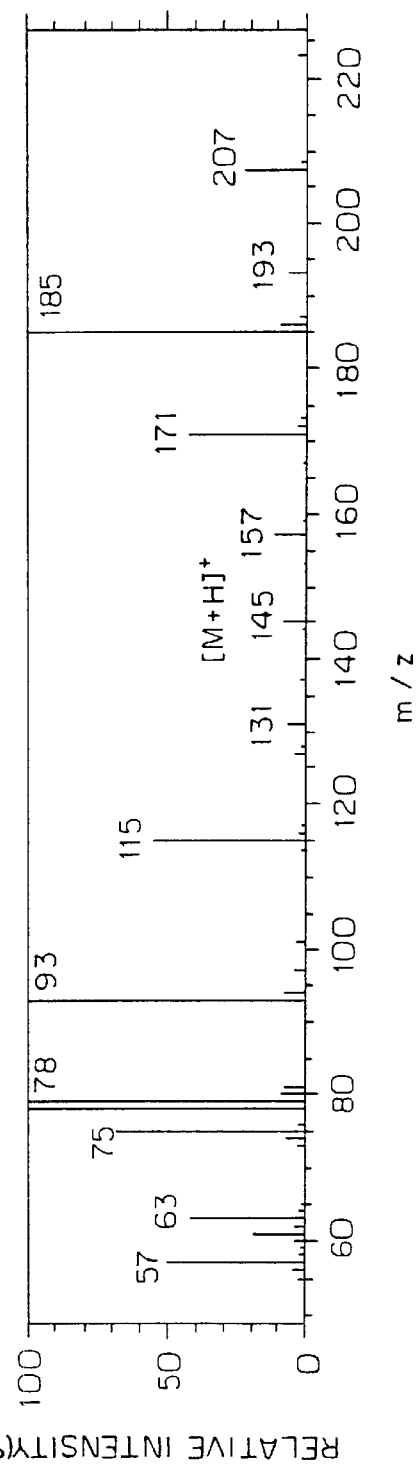
FIG. 2 illustrates the mass spectrum of the fraction at retention time of 4.05 to 4.16 minutes.
Figure 2B:
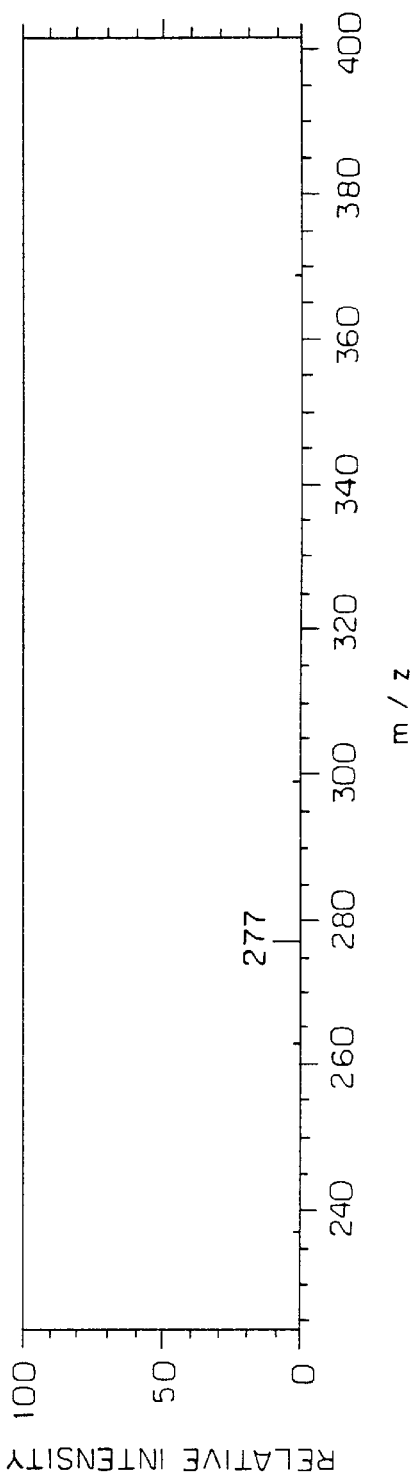
Figure 3:
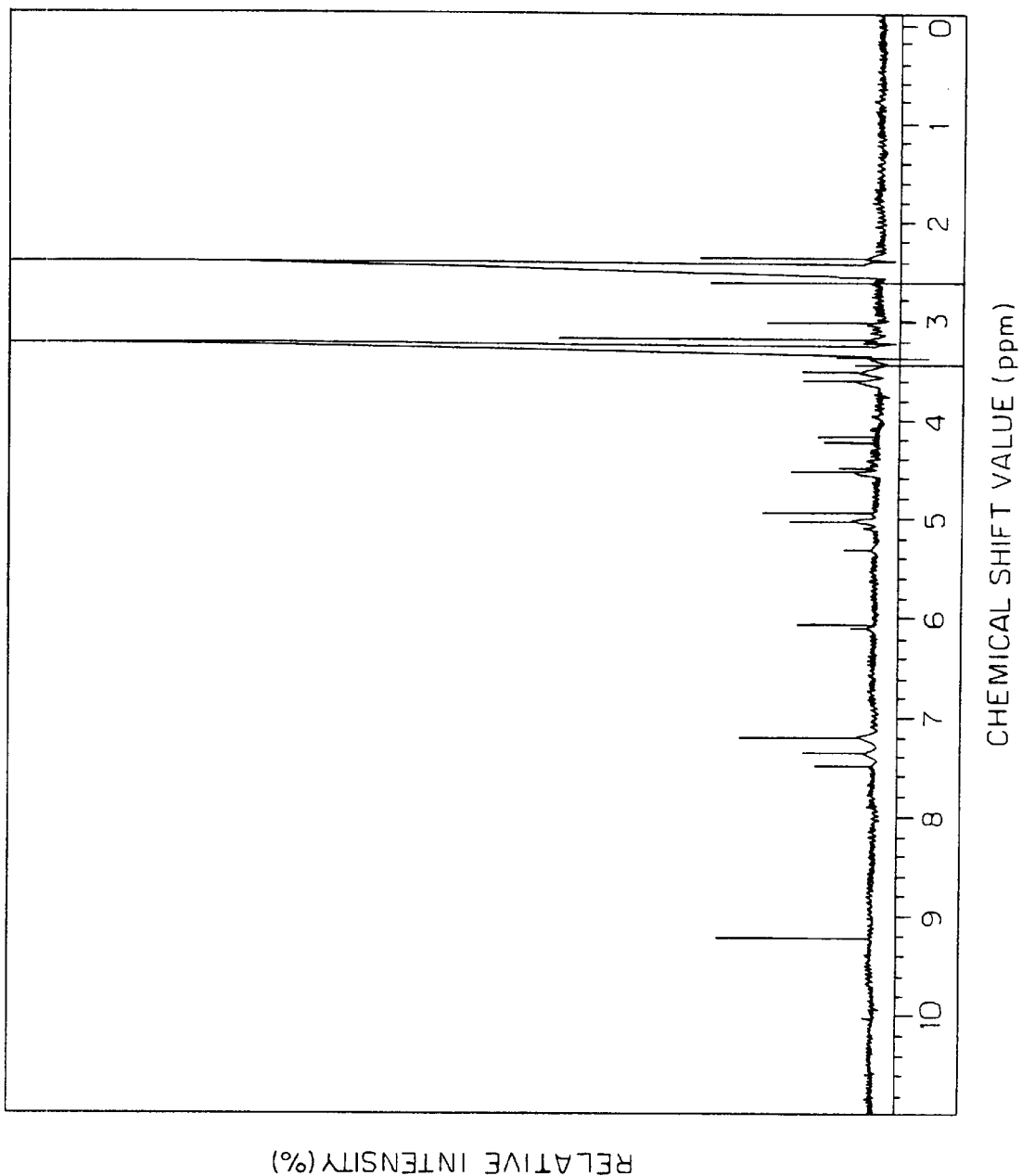
FIG. 3 illustrates the $^1$H-NMR spectrum of the fraction at retention time of 4.05 to 4.16 minutes.

The mass spectrum of the fraction at retention time of 4.05 to 4.16 minutes is illustrated in FIG. 2. The $^1$H-NMR spectrum of the fraction at retention time of 4.05 to 4.16 minutes is illustrated in FIG. 3. In FIG. 2, the horizontal axis represents m/z value and the vertical axis represents the relative intensity (%). In FIG. 3, the horizontal axis represents the chemical shift value (ppm) and the vertical axis represents the signal intensity.

FAB-MS: m/z 145 $[M+H]^+$

The sample was dissolved in dimethyl sulfoxide. Glycerol was used as a matrix for the measurements.

$^1$H-NMR: δ 3.50 (1H, m, 6-H), 3.59 (1H, m, 6-H), 4.52 (1H, m, 5-H), 4.95 (1H, d, J=5.0 Hz, 1-H), 5.02 (1H, t, J=6.0 Hz, H of 6-OH), 6.05 (1H, dd, J=2.5, 10.5 Hz, 3-H), 7.20 (1H, dd, J=1.5, 10.5 Hz, 4-H), 7.35 (1H, d, J=5.0 Hz, H of 1-OH)

The results are expressed assuming the chemical shift value of the residual proton of heavy dimethyl sulfoxide as 2.49 ppm.

The numbers for signal identification in $^1$H-NMR are as indicated in the following formula.

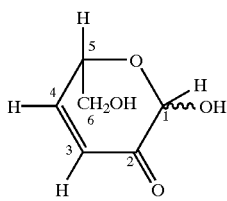

(I)

From these results, it revealed that the fraction at retention time of 4.05 to 4.16 minutes contained L-glycero-1,5-epoxy-1αβ,6-dihydroxy-cis-hex-3-en-2-one (hereinafter simply referred to as DGE).

Similarly, κ-carabiose was treated with alkali as described above in this Example. D-glycero-1,5-epoxy-1αβ,6-dihydroxy-cis-hex-3-en-2-one (hereinafter referred to as κ-DGE), which is an apoptosis-inducing substance, was purified from the alkali-treated preparation in the same manner as that described above.

(6) 45 g of agar powder (Nacalai Tesque) was suspended in 400 ml of distilled water. 4.1 ml of 11N HCl and distilled water to 450 ml were added to the suspension. The resulting acidic suspension was heated at 90° C. for 35 minutes. The heated acidic solution was neutralized with 10N NaOH. 2.7 ml of 1N NaOH was further added thereto. The solution was incubated under alkaline conditions at 37° C. for 15 minutes. The alkali-treated solution was neutralized with 1N HCl, and then concentrated to 150 ml using an evaporator. The concentrate was extracted with an equal volume of ethyl acetate ten times. The ethyl acetate phases from the ten rounds of extraction were collected, concentrated to 2 ml using an evaporator, and then dissolved in 20 ml of chloroform:methanol=9:1. The resulting solution was separated on silica column chromatography under the following conditions:column volume:250 ml; flow pressure:0.2 Kgf/cm$^2$; mobile phase solvent:chloroform:methanol=9:1; and fraction volume:8 ml. A portion of each fraction was analyzed on thin layer chromatography (developed with chloroform:methanol=9:1). Fractions 52 to 78 that only contain spots having Rf values of about 0.25 were collected as DGE-containing fractions, which were concentrated to 2 ml using an evaporator. The concentrate was subjected to the silica column chromatography again as described above. Fractions 64 to 96 were collected as DGE-containing fractions, concentrated using an evaporator, and then dissolved in 8 ml of distilled water. The aqueous DGE solution was lyophilized to obtain 113 mg of DGE preparation.

EXAMPLE 2

Apoptosis Induction Test (1) HL-60 cells were cultured at 37° C. in RPMI 1640 medium (Bio Whittaker) containing 10% of fetal bovine serum (JRH), which had been treated at 56° C. for 30 minutes, and suspended in RPMI 1640 medium at a concentration of $2.5 \times 10^5$ cells/4.5 ml.

500 μl of at 125 μM, 250 μM, 500 μM, 1 mM, 2 mM or 4 mM aqueous DGE solution was added to 4.5 ml of the suspension. The mixtures were incubated at 37° C. for 24 hours in the presence of 5% $CO_2$.

The cultured cells were examined under an optical microscope. Condensation of nuclei, shrinking of cells and formation of apoptotic bodies were observed for the cells cultured in the presence of DGE at a final concentration of 50 μM or more. No such phenomenon was observed for the control cells cultured with the addition of 500 μl of saline.

Measurement of apoptotic cells using FACScan as described in Saibo Kogaku, Bessatsu (Cell Technology, Suppl.) Jikken Protocol Series: Apoptosis Jikken Protocol (Experimental Protocol Series: Experimental Protocols for Apoptosis) (Shujun-sha) pp. 129–130 and analysis of DNA fragmentation as described in Bio Manual UP Series: Saishin Apoptosis Jikken-ho (Bio Manual UP Series: Current Experimental Methods for Apoptosis) (Yodo-sha) pp. 61–63 were carried out using cells cultured for 24 or 48 hours in the same manner as that described above. As a result, apoptotic cells were observed for cells cultured in the presence of DGE at a final concentration of 50 μM or more. DNA fragmentation was observed for cells cultured in the presence of DGE at a concentration of 50 or 100 μM. No such phenomenon was observed for the control cells cultured with the addition of 500 μl of saline.

(2) A portion of the cells cultured for 24 hours as described in Example 2-(1) was stained with 0.4% Trypan Blue and examined under an optical microscope. The number of viable cells which were not stained and the number of dead cells which were stained blue were counted. The concentration of DGE that results in a viability of 50% [Viability$_{50}$ (μM)] was determined to be 81.7 μM. As described above, DGE exhibited an antiproliferation activity against tumor cells due to the apoptosis-inducing activity. In addition, κ-DGE exhibited a similar activity.

EXAMPLE 3

Lipid Peroxide Radical Production Inhibition Test

*Staphylococcus aureus* 3A (National Collection of Type Culture, NCTC 8319) was inoculated into 5 ml of Brain Heart Infusion medium (Difco, 0037-17-8) and cultured at 37° C. overnight. The cells were collected by centrifugation, washed with phosphate buffered saline three times and then suspended in phosphate buffered saline at a concentration of $1 \times 10^7$ colony forming units/ml. A mixture of 100 μl of the cell suspension, 100 μl of the aqueous DGE solution at 10 or 100 mM, 100 μl of 1 mg/ml aqueous methemoglobin solution (Sigma, M9250), 600 μl of phosphate buffered saline and 100 μl of 50 mM aqueous tert-butyl hydroperoxide solution (Katayama Kagaku, 03-4 990) were reacted at 37° C. for 30 minutes. 1 ml of 2×NMP medium was added to the reaction mixture to stop the reaction. 2×NMP was prepared as follows: 8 g of Nutrient Broth (Difco, 0003-01-6), 5 g of Trypton (Difco, 0123-17-3), 5 g of NaCl, 10 g of mannitol (Nacalai Tesque, 213-03) and 0.035 g of phenol red (Nacalai Tesque, 268-07) were dissolved in distilled water to make the volume to 500 ml; the pH was adjusted to 7.4 with NaOH; and the mixture was then sterilized by filtration to obtain 2×NMP medium. The resultant mixture was diluted every 3-folds with NMP medium (prepared by diluting 2×NMP medium 2-folds with sterilized water) to prepare 12 serial dilutions. 160 μl of each dilution was placed in each well of a 96-well microtiter plate. The plate was incubated at 37° C. overnight. Color of the medium was observed with the naked eye. The sample that resulted in the change of color of the medium in the well from red to yellow as a result of the growth of bacteria was identified as having an activity of inhibiting lipid peroxide radical production.

The results are shown in Table 1. In Table 1, + represents the sample for which the growth of the bacterium in the well was observed, and − represents the sample for which the growth of the bacterium in the well was not observed. The number at the upper line in the Table represents the concentration of DGE in the reaction mixture that was reacted with tert-butyl hydroperoxide and the cells at 37° C. for 30 minutes.

TABLE 1

| DGE | 1 mM | 10 mN |
|---|---|---|
| Growth of bacteria | − | + |

As seen from these results, DGE exhibited an activity of inhibiting lipid peroxide radical production. In addition, similar activities were observed for κ-DGE and DGE-GSH described below.

EXAMPLE 4

NO Production Inhibition Test (1) RAW264.7 cells (ATCC TIB 71) were suspended in Dulbecco's modified Eagle's medium (Bio Whittaker, 12-917F) without phenol red containing 10% fetal bovine serum (Gibco) and 2 mM L-glutamine (Life Technologies Oriental, 25030-149) at a concentration of $3 \times 10^5$ cells/ml. 500 µl of the suspension was added to each well of a 48-well microtiter plate and the plate was incubated at 37° C. for 12 hours in the presence of 5% $CO_2$. 10 µl of an aqueous solution containing 25 µg/ml lipopolysaccharide (LPS, Sigma, L-2012) and 500 U/ml interferon-γ (IFN-γ, sold by Cosmobio, GZM-MG-IFN), and 10 µl of the aqueous DGE solution at 250 or 500 µM were added to the well. The plate was incubated for additional 12 hours. The concentration of $NO_2^-$ produced by oxidation of NO in the medium was then measured. As control groups, a group to which LPS or IFN-γ was not added and a group to which DGE was not added were provided.

After cultivation, 100 µl of 4% Griess' reagent (Sigma, G4410) was added to 100 µl of the medium, and the mixture was allowed to stand for 15 minutes at room temperature. The absorbance at 490 nm was then measured. $NO_2^-$ concentration in the medium was calculated with reference to a calibration curve prepared by using $NaNO_2$ at a given concentration dissolved in the same medium as that described above. All of the measurements were carried out in triplicate.

Figure 4:
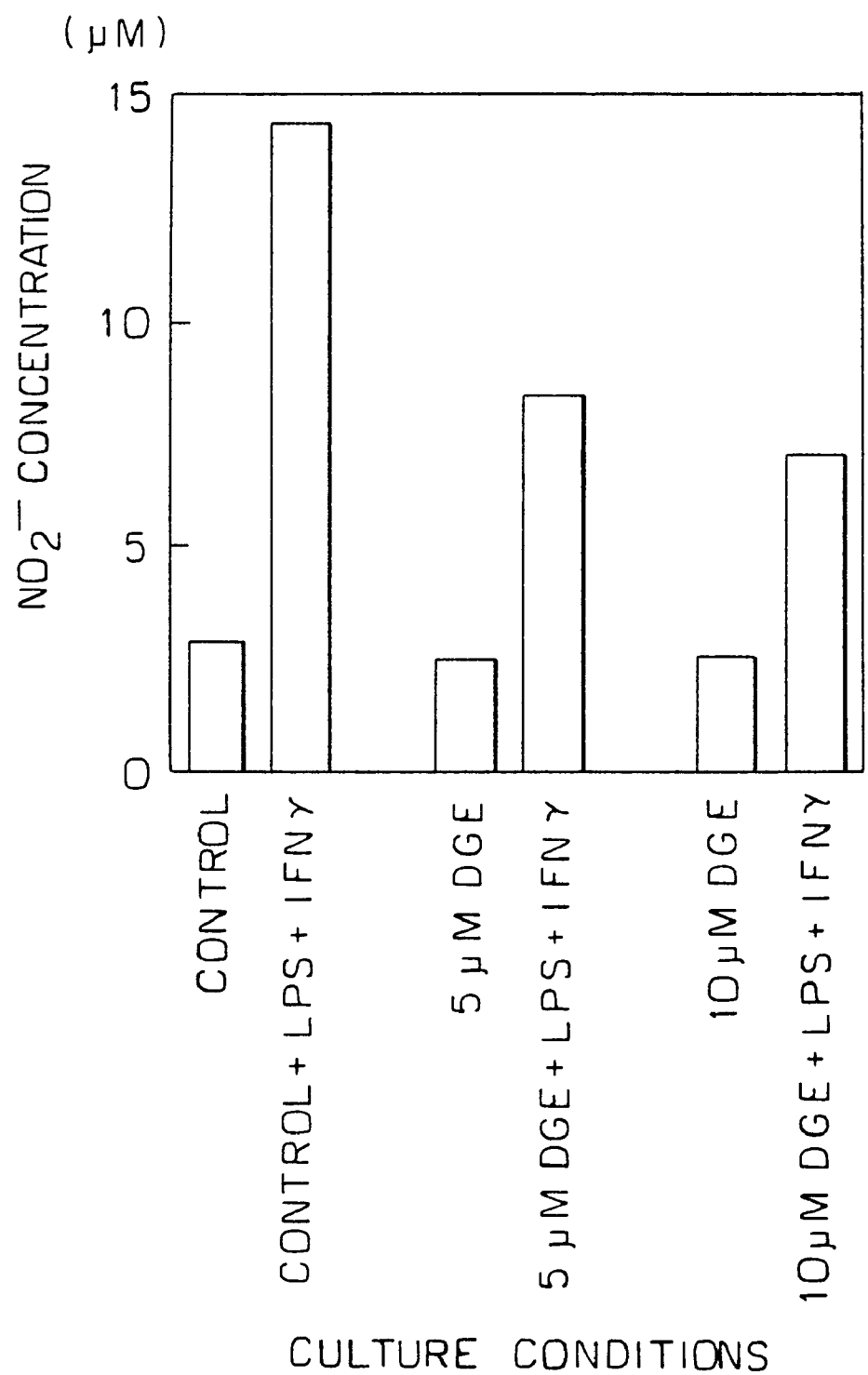
FIG. 4 illustrates the $NO_2^-$ concentration in a medium obtained by culturing under various culture conditions in the presence of DGE.

As a result, DGE dose-dependently inhibited NO production induced by LPS and IFN-γ. The results are shown in FIG. 4. FIG. 4 illustrates the $NO_2^-$ concentration in the medium incubated under the respective culture conditions in the presence of DGE. In FIG. 4, the horizontal axis the represents the culture conditions and the vertical axis represents the $NO_2^-$ concentration (µM).

RNA was prepared from RAW264.7 cells cultured for 4, 6 or 8 hours under conditions similar to those described above. The amount of mRNA encoding inducible NO synthase [iNOS; Biochem. Byophys. Res. Commun., 215:148–153 (1995)] contained in the RNA was determined by the RT-PCR method. As a result, amplification of a DNA fragment from the iNOS mRNA was observed for the control cells to which the aqueous DGE solution was not added. On the other hand, no amplification of the fragment was observed for the cells to which the aqueous DGE solution was added. These results suggest that the inhibition of NO production by DGE is caused via the inhibition of iNOS transcription.

(2) RAW264.7 cells were suspended in Dulbecco's modified Eagle's medium without phenol red containing 10% fetal bovine serum and 2 mM L-glutamine at a concentration of $3 \times 10^5$ cells/ml. 500 µl of the suspension was placed in each well of a 48-well microtiter plate. The plate was incubated for 37° C. for 6 hours in the presence of 5 % $CO_2$. 10 µl of aqueous solution, which was prepared by dissolving DGE at a concentration of 0.5 mM in water and sterilizing it by filtration, was added to the well. The plate was incubated for additional 0.5 or 5 hours. 10 µl of an aqueous solution containing 5 µg/ml LPS and 2000 U/ml IFN-γ was then added to the well. The plate was incubated for additional 12 hours. The concentration of $NO_2^-$ produced by oxidation of NO in the medium was measured. As control groups, a group to which LPS or IFN-γ was not added and a group to which DGE was not added were provided.

After cultivation, 100 µl of 4% Griess' reagent was added to 100 µl of the culture supernatant, and the mixture was allowed to stand for 15 minutes at room temperature. The absorbance at 490 nm was then measured. $NO_2^-$ concentration in the medium was calculated with reference to a calibration curve prepared by using $NaNO_2$ at a given concentration dissolved in the same medium as that described above.

All of the measurements were carried out in triplicate.

As a result, a stronger inhibition of NO production by was observed for the group cultured for 5 hours in the presence of DGE before the addition of LPS and IFN-γ as compared with the group cultured for 0.5 hour.

Figure 5:
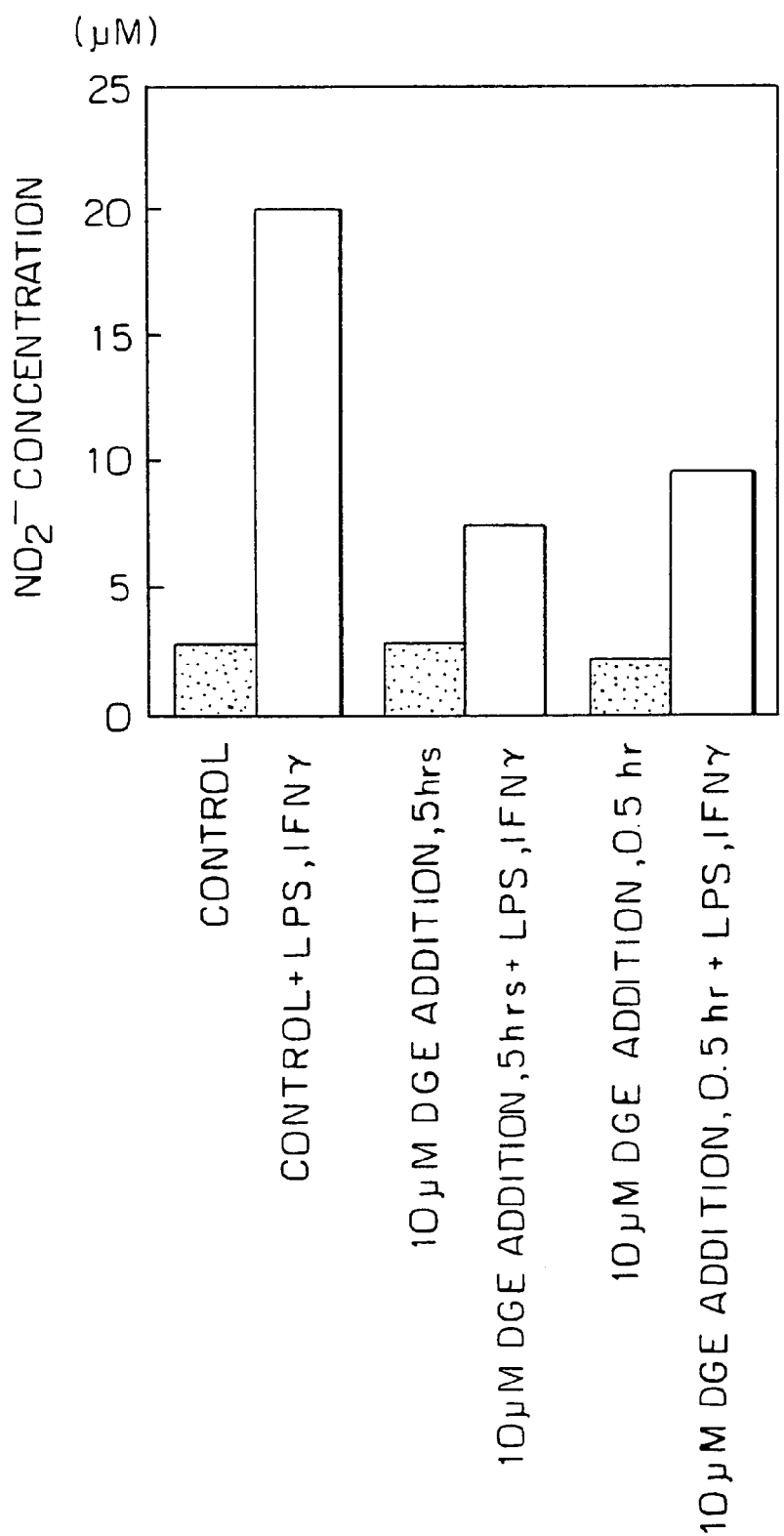
FIG. 5 illustrates the $NO_2^-$ concentration in a medium obtained by incubating under various culture conditions in which DGE is added during the pre-culture.

The results are shown in FIG. 5. FIG. 5 illustrates the $NO_2^-$ concentration in the medium obtained by incubating under various culture conditions in which DGE was added during the pre-culture. In FIG. 5, the horizontal axis represents the culture conditions and the vertical axis represents the $NO_2^-$ concentration (µM).

As described above, DGE exhibited an activity of inhibiting NO production. In addition, κ-DGE exhibited a similar activity.

EXAMPLE 5

Antimicrobial Activity Test

The antimicrobial activities of DGE against *Escherichia coli* W3110 (Bacterium 1), *Salmonella typhimurium* LT2 (Bacterium 2), *Bacillus subtilis* IFO3021 (Bacterium 3), *Pseudomonas aeruginosa* IFO3080 (Bacterium 4) and *Streptococcus mutans* GS5 (Bacterium 5) were examined as follows.

The Bacteria 1 to 4 were cultured overnight in L-broth. The cultures were diluted to a concentration of about $2 \times 10^5$ cells/180 µl with Sensitive Bouillon medium (Nissui) base on the turbidity. The Bacterium 5 was cultured overnight in Brain Heart Infusion medium. The culture was diluted to a concentration of about $2 \times 10^5$ cells/180 µl with Brain Heart Infusion medium based on the turbidity. 180 µl of each bacterial dilution was placed in each well of a 96-well microtiter plate. On the other hand, the respective bacterial dilutions were further diluted and spread onto plates of L-broth or Brain Heart Infusion medium. The plates were incubated at 37° C. overnight. The resulting colonies were counted to determine the stating viable cell numbers.

A 14.4 mg/ml DGE solution was diluted every 2-folds to prepare serial dilutions. 20 µl each of the dilutions was placed in the well in which the bacterial dilution had been placed. The cells were cultured at 37° C. for 24 hours without shaking. After cultivation, the turbidity of each culture was measured. The concentration of the sample in the well that resulted in turbidity lower than that of a control to which saline was added was defined as the minimal growth-inhibitory concentration.

Furthermore, the culture from the well for which the growth of bacterial cells was not observed was spread onto plates. After the plates were incubated at 37° C. overnight, the colony number was counted to determine the viable cell number. The concentration of the sample in the culture that resulted in a lower viable cell number after 24-hours' cultivation without shaking from the addition of the sample as compared with the starting viable cell number measured beforehand was defined as the minimal bacteriocidal concentration. The minimal growth-inhibitory concentrations and the minimal bacteriocidal concentrations of DGE for the Bacteria 1 to 5 were determined as shown in Table 2.

TABLE 2

|  | Minimal growth-inhibitory concentration ($\mu$g/ml) | Minimal bacteriocidal concentration ($\mu$g/ml) |
| --- | --- | --- |
| Bacterium 1 | 360 | 720 |
| Bacterium 2 | 360 | 720 |
| Bacterium 3 | 360 | 720 |
| Bacterium 4 | 360 | 720 |
| Bacterium 5 | 90 | 180 |

As described above, DGE exhibited an antimicrobial activity. In addition, κ-DGE and DGE-GSH described below also exhibited similar activities.

EXAMPLE 6

Antimutagenic Activity Test

An antimutagenic activity was determined according to a method for detecting an environmental mutagen by the umu test, which can determine mutagenicity with reference to the β-galactosidase activity (Mutation Research, 147: 219 (1985)). Briefly, 25 $\mu$l of mutagen [mitomycin C (a DNA crosslinker) at 10 $\mu$g/ml or 4-nitroquinoline-1-oxide (NQO, a DNA methylating agent) at 7 $\mu$g/ml] was added to 50 $\mu$l of DGE solution at a varying concentration (1.0, 5.0, 10 or 15 mM). A culture of *Salmonella typhimulium* TA1535/pSK1002 in TGA medium at OD600 of 0.12 was added to the mixture to make the final volume to 1.5 ml. The mixture was then incubated at 37° C. for 2 hours with shaking. 200 $\mu$l of the culture was used to measure the β-galactosidase activity according to the method of Miller [Experiments in molecular genetics, pp. 352 (1972)]. The results are shown in Table 3.

TABLE 3

| | β-Galactosidase activity | | | | |
| --- | --- | --- | --- | --- | --- |
| | Final concentration of DGE (mM) | | | | |
| | 0 | 0.03 | 0.17 | 0.33 | 0.5 |
| Mitomycin C | 611 | 590 | 570 | 451 | 383 |
| NQO | 1437 | 1376 | 1212 | 1038 | 926 |

As seen from the Table, DGE at a final concentration of 0.5 mM exhibited an antimutagenic activity of 37% against mitomycin C, a DNA crosslinker, and 36% against NQO, a methylating agent, respectively. In addition, κ-DGE and DGE-GSH described below also exhibited similar activities.

EXAMPLE 7

Carcinostatic Activity Test (1) Agar powder (Wako Pure Chemical Industries) was added to 50 mM citric acid solution to a final concentration of 3%. The mixture was heated at 95° C. for 160 minutes, treated with alkali at pH 12 and then neutralized upon use to prepare a test solution for a carcinostatic activity test.

Male nude mice (SPF/VAFBalb/cAnNCrj-nu, 4 weeks old) were purchased from Nippon Charles River and pre-bred for 1 week. Human colon cancer cell line HCT116 (ATCC CCL-247) were transplanted subcutaneously to the mice at $1.5 \times 10^6$ cells/mouse.

After 2 weeks from the transplantation of the colon cancer cell line, the test solution for the carcinostatic activity test, which was adjusted to pH 6.5 immediately before use, was freely given to the mice as drinking water for 5 days per week. The average volume of the daily intake of the solution per mouse was 3.5 ml. Furthermore, MF from Oriental Yeast was freely given to the mice as feed.

After 4 weeks from the beginning of administration of the test solution, solid cancer was removed from each mouse that received the test solution and the weight of the solid cancer was compared with that from a control mouse to which normal water was given. This test was carried out using 10 mice per group.

As a result, a significant inhibition of cancer growth was observed in the group that orally received the test solution for the carcinostatic activity test.

(2) Ehrlich's carcinoma cells were administered to 18 female ddY mice (5 weeks old, weighing about 25 g) intraperitoneally ($1.2 \times 10^6$ cells/mouse). Observation was continued for 30 days. The average days of survival, the prolongation rate and the 30-day survival number were then calculated. Mice were divided into 3 group each consisting of 6 mice. One was a control group, and other two groups received DGE at 2 mg/kg and 20 mg/kg, respectively. DGE was intraperitoneally administered for 4 days from the day after the administration of cancer.

The results are shown in Table 4. The average days of survival were 14.3 days for the control group. The 30-day survival numbers were 1 and 3 for the groups that received DGE at 2 mg/ml and 20 mg/kg, respectively. For the groups that received DGE at 2 mg/ml and 20 mg/kg, the average days of survival were 23.7 days and 28.0 days, and the prolongation rates were 141% or more and 195% or more, respectively. Thus, a significant prolongation effect was observed.

TABLE 4

|  | Average days of survival (days) | Prolongation rate (%) | 30-day survival number |
| --- | --- | --- | --- |
| Control | 14.3 | 100 | 0 |
| DGE at 2 mg/kg | 23.7 | >141 | 1 |
| DGE at 20 mg/kg | 28.0 | >195 | 3 |

As described above, DGE exhibited a carcinostatic activity. In addition, κ-DGE and DGE-GSH described below also exhibited similar activities.

EXAMPLE 8

Melanogenesis Inhibition Test

Mouse melanoma cell B16BL6 suspended in RPMI 1640 medium containing 10% fetal bovine serum was dispensed into a 6-well plate at $5\times10^4$ cells/well/2 ml medium and the plate was incubated at 37° C. On the 2nd day, 100 µl of a DGE solution (2 mg/ml to 0.2 mg/ml) was added thereto. On the 7th day, the medium was exchanged and, at the same time, 100 µl of the DGE solution (2 mg/ml to 0.2 mg/ml) was added thereto. On the 8th day, the cells were harvested. After DNA, RNA and protein were digested, the absorbance at 400 nm was measured to determine an activity of inhibiting melanogenesis.

Briefly, after removing the medium by aspiration, 0.3 ml of 0.25% trypsin dissolved in 20 mM EDTA solution was added to each well and the plate was incubated at 37° C. for 10 minutes. 2 ml of fresh medium was then added to the well and the cells were suspended. The suspension was transferred to a tube. After the medium was removed by centrifugation, the cells were suspended in 2 ml of PBS and centrifuged again. After the supernatant was removed, 30 µl of 50 mM sodium acetate buffer (pH 5.0) containing 5 mM manganese chloride and 1 µl of 70,000 U/ml DNase I (Takara Shuzo) were added to the cells. The mixture was mixed thoroughly and then incubated at 37° C. for 2 hours to digest DNA. 1 µl of 10 mg/ml ribonuclease A (Sigma) was then added to the mixture and the resultant mixture was incubated at 50° C. for 1 hour to digest RNA. Finally, 100 mM Tris-hydrochloride buffer (pH 7.8) containing 100 µg/ml proteinase K (Sigma), 0.1% Triton X and 10 mM EDTA was added thereto to make the total volume to 200 µl for $2\times10^6$ cells. After the mixture was incubated at 37° C. for 16 hours, the absorbance at 400 nm was measured.

As a result, an activity of inhibiting melanogenesis was observed for DGE, confirming the whitening effect thereof. In addition, κ-DGE and DGE-GSH described below also exhibited similar activities.

EXAMPLE 9

α-Glucosidase Inhibition Test (1) The activity of inhibiting α-glucosidase of DGE was measured by reacting p-nitrophenyl-α-D-glucopyranoside, a chromogenic substrate for α-glucosidase, with α-glucosidase from yeast and calorimetrically quatifying 4-nitrophnol released by hydrolysis. Briefly, 10 µl of α-glucosidase solution [40 mU/ml, derived from *S. cerevisiae*, Sigma, dissolved in 10 mM phosphate buffer (pH 7.2 at 37° C.)] and 10 µl of a solution containing a test sample dissolved in 10 mM phosphate buffer (pH 7.2 at 37° C.) were mixed. 80 µl of a 1.5 mg/ml substrate solution [Sigma, dissolved in 10 mM phosphate buffer (pH 7.2 at 37° C.) was added thereto to initiate the reaction. After reacting at 37° C. for 40 minutes, the absorbance at 410 nm was measured (Shimadzu uv2200). The results are shown in Table 5. The remaining activity therein was calculated defining the activity without the test sample as 100%.

TABLE 5

| Amount of DGE added (µM) | Absorbance (OD 410 nm) | Remaining activity (%) |
|---|---|---|
| 0 | 0.444 | 100 |
| 5 | 0.433 | 98 |
| 50 | 0.401 | 90 |
| 500 | 0.221 | 50 |
| 1000 | 0.114 | 26 |
| 5000 | 0.083 | 19 |

As seen from these results, DGE exhibits the activity of inhibiting α-glucosidase. The concentration of DGE that inhibits α-glucosidase activity by 50% ($IC_{50}$) was 500 µM.

(2) A crude enzyme preparation of α-glucosidase from rat small intestine mucous membrane [prepared according to the method as described in Arne Dahlqvist, Anal. Biochem., 7:18–25 (1964)] was used to measure the activity of inhibiting α-glucosidase of DGE as follows.

For the enzymatic reaction, 80 µl of a solution of sucrose, maltose, treharose or soluble starch as a substrate in 10 mM phosphate buffer (pH 7.0) buffer at a final concentration of 100 mM (0.5% for soluble starch) was added to 10 µl of a test sample solution appropriately diluted with the same buffer. 10 µl of the crude enzyme solution prepared from rat small intestine was added thereto. The mixture was reacted at 37° C. for 20 minutes.

The enzymatic reaction was assessed by adding 3 ml of a reagent for glucose measurement (Wako Pure Chemical Industries) to the reaction mixture, reacting at 37° C. for 5 minutes and then measuring the absorbance at 505 nm as the glucose content in the mixture.

The inhibitory activity of DGE on the digestion of each substrate by α-glycosidase was measured using DGE at four different concentrations according to the above-mentioned method. The activity of inhibiting α-glycosidase was expressed as a relative activity (%) defining the activity of the control without DGE as 100%.

The results are shown in Table 6.

TABLE 6

| | DGE (mM) | | | |
|---|---|---|---|---|
| | 0.2 | 0.5 | 1.0 | 2.0 |
| Sucrose | 91 | 92 | 83 | 71 |
| Maltose | 96 | 97 | 100 | 96 |
| Treharose | 98 | 96 | 99 | 100 |
| Soluble starch | 100 | 95 | 91 | 92 |

The inhibition constant (Ki) of DGE for sucrose as determined using Dixon plot was 6.0 mM.

When sucrose was used as a substrate, DGE exhibited a higher activity of inhibiting α-glycosidase than that observed when using maltose or the like. In addition, κ-DGE and DGE-GSH described below also exhibited similar activities of inhibiting α-glycosidase.

EXAMPLE 10

Antirheumatic Activity Test

DSEK cell is a fibroblast cell line established from a synovial membrane of a human patient with chronic rheumatism and is held at Department of Second Internal Medicine, Integrated Medical Center, Saitama Collage of Medicine as an in vitro rheumatoid model. DSEK cells were cultured in Iscov-MEM medium (IMDM: Gibco-BRL) containing 10% FBS (Bio Whittaker) at 37° C. in the presence of 5% $CO_2$ to confluence. The cells were suspended in the same medium at a concentration of $3\times10^4$ cells/ml using a trypsin-EDTA solution (Bio Whittaker). 200 µl of the suspension was dispensed into each well of a 96-well microtiter plate (Falcon). After culturing for 5 to 7 days at which time the cells grew to 80% confluence, the medium was changed to 200 µl of the above-mentioned medium containing DGE at a 25, 50, 75, 100, 200 or 400 µM.

After incubating for 24 or 72 hours, 10 µl of Premix WST-1 (Takara Shuzo, MK400) was added to the well. The mixture was reacted at 37° C. for 3.5 hours. The degree of cell growth was expressed by a value obtained by subtracting the absorbance at 650 nm ($A_{650}$) from the absorbance at 450 nm ($A_{450}$).

The results are shown in Table 7.

TABLE 7

| DGE concentration (µM) | Culture period | |
|---|---|---|
| | 24 hours | 72 hours |
| | Degree of cell growth ($A_{450-650}$) | |
| 0 | 3.98 | 3.94 |
| 25 | 3.86 | 3.33 |
| 50 | 3.24 | 3.25 |
| 100 | 2.88 | 2.05 |
| 200 | 1.26 | 0.48 |
| 400 | 0.71 | 0.35 |

The concentrations that result in the inhibition of the growth of half-cells ($IC_{50}$) as determined on the basic of the $A_{450-650}$ data were 207 µM at 24 hours and 112 µM at 72 hours, respectively.

As described above, in the in vitro rheumatoid model (DSEK cells), the growth of the rheumatoid cells was strongly inhibited in the wells to which DGE was added as compared with the control wells to which PBS was added. Furthermore, it was recognized that the compound not only maintains its growth inhibitory activity but also tends to enhance the activity over time.

These results demonstrate that DGE has a strong antirheumatic activity. Therefore, it is expected that DGE would be developed as therapeutic agents and healthy foods effective against chronic rheumatism. In addition, κ-DGE and DGE-GSH described below also exhibited similar activities.

150 µl/well of culture supernatant was recovered from the DSEK cell culture at 24 or 72 hours. The effects of DGE on the production (expression) of cytokines (human TGF-β, human FGF-β, human IL-1α and human IL-10) from the cell were determined using ELISA kits specific for the respective cytokines (from Intergen for human FGF-β and human IL-10; and from Promega for human IL-1α and human TGF-β).

As a result, DGE exhibited activities of inhibiting the production of human IL-1α and human FGF-β, as well as enhancing the production of human IL-10 and human TGF-β.

EXAMPLE 11

Prostaglandin $E_2$ Production Inhibition Test

RAW264.7 cells were suspended in Dulbecco's modified Eagle's medium containing 10% fetal bovine serum at a concentration of $3\times10^5$ cells/ml. 500 µl of the suspension was added to each well of a 48-well microtiter plate and the plate was incubated at 37° C. for 6 hours in the presence of 5% $CO_2$. 10 µl of an aqueous solution prepared by dissolving DGE at a concentration of 0.5 mM in water and sterilizing it by filtration was added to the well. The plate was incubated for additional 0.5 or 5 hours. 10 µl of 50 µg/ml aqueous LPS solution was then added to the well. After the plate was incubated for additional 12 hours, the amount of prostaglandin $E_2$ was measured. As control groups, a group to which LPS was not added and a group to which DGE was not added were provided.

After cultivation, the amount of prostaglandin $E_2$ in the culture supernatant was measured using Prostaglandin $E_2$ ELISA Kit (Neogen, Code. 404110). All of the measurements were carried out in triplicate.

Figure 6:
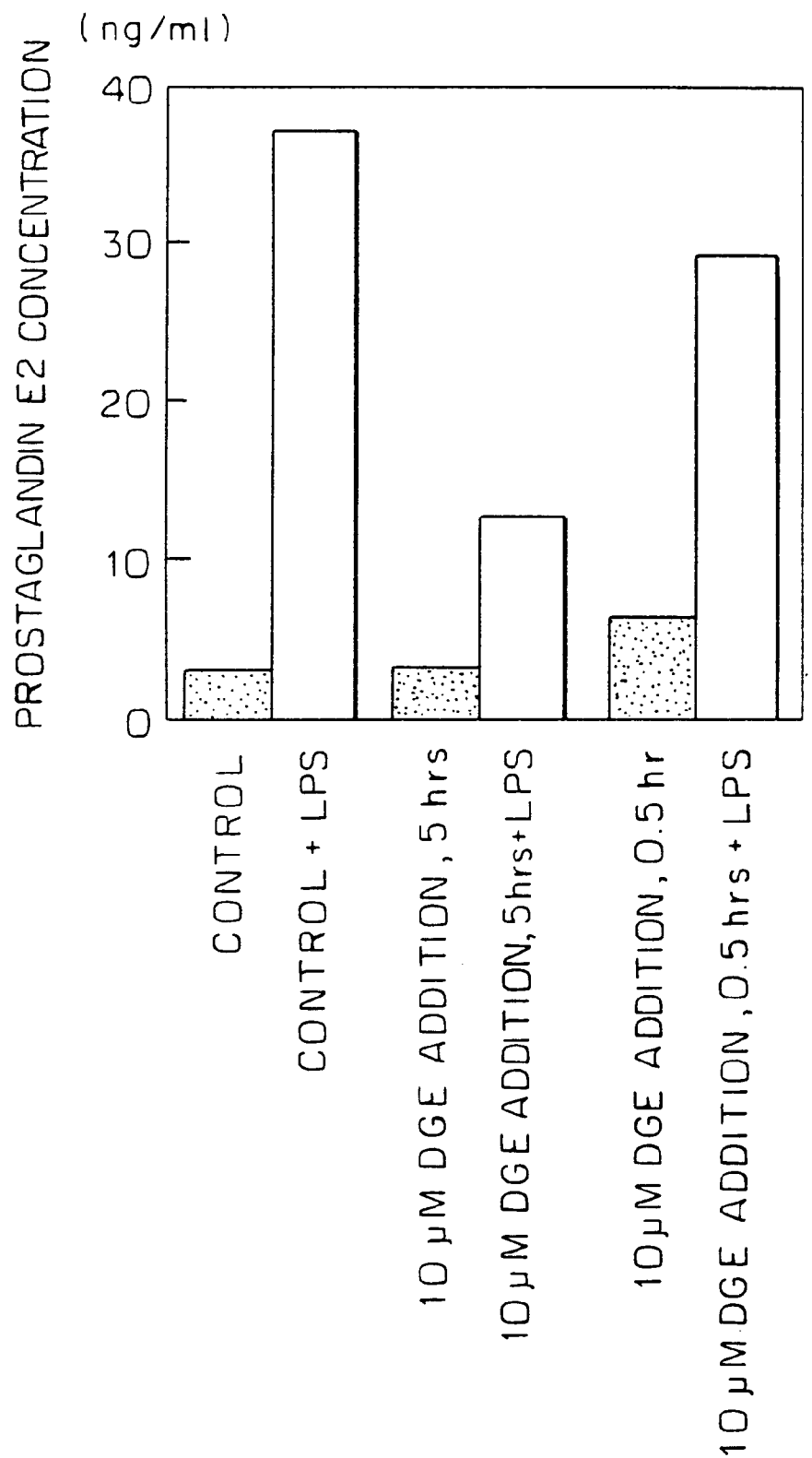
FIG. 6 illustrates the prostaglandin $E_2$ concentration in a medium obtained by incubating under various culture conditions in which DGE is added during the pre-culture.

The results are shown in FIG. 6. FIG. 6 illustrates the prostaglandin $E_2$ concentration in the medium obtained by incubating under various culture conditions in which DGE is added during the pre-culture. In FIG. 6, the horizontal axis represents the culture conditions and the vertical axis represents the prostaglandin $E_2$ concentration (ng/ml).

As a result, DGE inhibited the prostaglandin $E_2$ production induced by LPS. In addition, stronger inhibition of prostaglandin $E_2$ production was observed for wells incubated for 5 hours in the presence of DGE before the addition of LPS as compared with that incubated for 0.5 hour.

EXAMPLE 12

Heat Shock Protein Induction Test 5 ml of RPMI 1640 medium containing 10% fetal bovine serum and HL-60 cells at a concentration of $2\times10^5$ cells/ml was placed in each well of a 6-well plate. The plate was incubated at 37° C. for 24 hours in the presence of 5% $CO_2$. DGE at a final concentration of 0, 6.25, 12.5, 25, 50 or 100 µM was then added thereto. The incubation was continued for additional 6 hours.

After cultivation, the cell number was counted.

The cells were harvested by centrifugation, washed with PBS to prepare DGE-treated cells. Cells that were cultured in the same manner after heated at 45° C. for 10 minutes were also prepared.

These treated cells were used for SDS-PAGE according to the method as described in Molecular Cloning [Cold Spring Harbor Laboratory Press (1989)]. The treated cells were suspended in SDS-PAGE Sample buffer at a concentration of $2.5\times10^6$ cells/ml. The cell suspensions were treated at 100° C. for 10 minutes. 5 µl each of the cell suspensions was applied to two SDS-PAGE gels (5% stacking gel, 10% separation gel) and electrophoresed. One of the gels was subjected to Coomassie staining. The other gel was blotted onto a polyvinylidene difluoride transfer membrane [Immobilon™, Millipore, Cat. # IPVH000-10]. The membrane was blocked at 4° C. overnight using Block Ace (Dainippon Pharmaceutical, Cat. # UK-B25).

The blocked membrane was reacted with a monoclonal antibody HSP72/73(Ab-1) (Oncogene Research Products, Cat. # HSP01), which specifically reacts with heat-inducible 70-kDa heat shock protein. The membrane was washed with TBS containing 0.05% Tween 20 followed by TBS. The membrane was then reacted with a peroxidase-conjugated secondary antibody HRT-rabbit anti-mouse IgG (H+L) (Zymed Laboratories, Inc., Cat. # 61-6520), and then washed as described above. The membrane reacted with the primary and secondary antibodies was reacted with a chemiluminol reagent, Renaissance™ (Dupont NEN, Cat. # NEL-100). The membrane was then exposed to an X-ray film to confirm the induction of 70-kDa heat shock protein.

As a result, the induction of 70-kDa heat shock protein by DGE was observed. The degree of the induction is shown in Table 8. In Table 8, + represents the induction level. Increased number of + means increased induction. On the other hand, − means that no induction was observed.

In addition, κ-DGE and DGE-GSH described below also exhibited similar activities of inducing heat shock protein.

TABLE 8

| Treatment of cells | Induction of heat shock protein |
|---|---|
| Heating at 45° C. for 10 min. | +++ |
| 0 µM DGE | − |
| 6.25 µM DGE | + |
| 12.5 µM DGE | + |
| 25.0 µM DGE | ++ |
| 50.0 µM DGE | +++ |
| 100 µM DGE | ++++ |

EXAMPLE 13

Preparation of 5-L-glutathion-S-yl-2-hydroxy-3,7-dioxabicyclo[2.2.2]octan-1-ol (DGE-GSH)

(1) DGE and reduced glutathione (GSH; Nacalai Tesque) were dissolved in PBS at concentrations of 20 mM and the mixture was reacted at 37° C. overnight. 100 µl of the reaction mixture was fractionated on a normal phase column, PAL-PAK Type S. Chromatography was carried out under the following conditions: flow rate: 1 ml/min.; 90% aqueous acetonitrile solution containing 0.1% TFA (0 to 10 min.); linear gradient from 90% aqueous acetonitrile solution containing 0.1% TFA to 50% aqueous acetonitrile solution containing 0.1% TFA (10 to 50 min.); detection: absorbance at 195 nm; collection of fractions: every 1.5 min. The respective fractions were concentrated to dryness and redissolved in 50 µl of distilled water. Antiproliferatrion activities against tumor cells were measured using HL-60 cells as described in Example 1-(2). As a result, apoptotic bodies were observed for groups to which fractions around 30 to 40 were added. The absorbance at 590 nm of these groups was lower than that of the control group to which water was added, indicating the inhibition of cell growth. 50 µl of an active fraction prepared in the same manner as that described above was fractionated on reverse phase chromatography (TSKgel ODS-80Ts (5 µm), Toso, 4.6×250 mm). Chromatography was carried out under the following conditions: flow rate: 1 ml/min.; distilled water containing 0.1% TFA (0 to 15 min.); linear gradient from distilled water containing 0.1% TFA to 50% aqueous acetonitrile solution containing 0.1% TFA (15 to 30 min.); 50% aqueous acetonitrile solution containing 0.1% TFA (30 to 45 min.); detection: absorbance at 215 nm; collection of fractions: every 1.5 min. The respective fractions were concentrated to dryness and redissolved in 50 µl of distilled water. Antiproliferatrion activities against tumor cells were measured using HL-60 cells as described in Example 1-(2). As a result, apoptotic bodies were observed for groups to which fractions around 4 to 9 were added. The absorbance at 590 nm of these groups was lower than that of the control group to which water was added, indicating the inhibition of cell growth. These results demonstrate the apoptosis-inducing activity.

The above-mentioned normal phase chromatography was repeated ten times. Fractions having apoptosis-inducing activities were collected, concentrated to dryness, redissolved in 1 ml of distilled water and then subjected to normal phase chromatography to prepare purified fractions. The fractions purified by the normal phase chromatography were then applied to the above-mentioned reverse phase chromatography. Fractions having apoptosis-inducing activities were collected and concentrated to dryness. As a result, 5 mg of a compound having an apoptosis-inducing activity was obtained from 1 ml of the reaction mixture containing 20 mM DGE and 20 mM glutathione.

This compound was used for structure determination.

(2) Mass spectrometric analysis of the apoptosis-inducing substance obtained in Example 13-(1), i.e., the product of reaction between DGE and glutathione, was carried out using DX302 mass spectrometer. Furthermore, the sample was dissolved in heavy water to analyze the structure by nuclear magnetic resonance (NMR). The results are shown below.

Figure 7A:
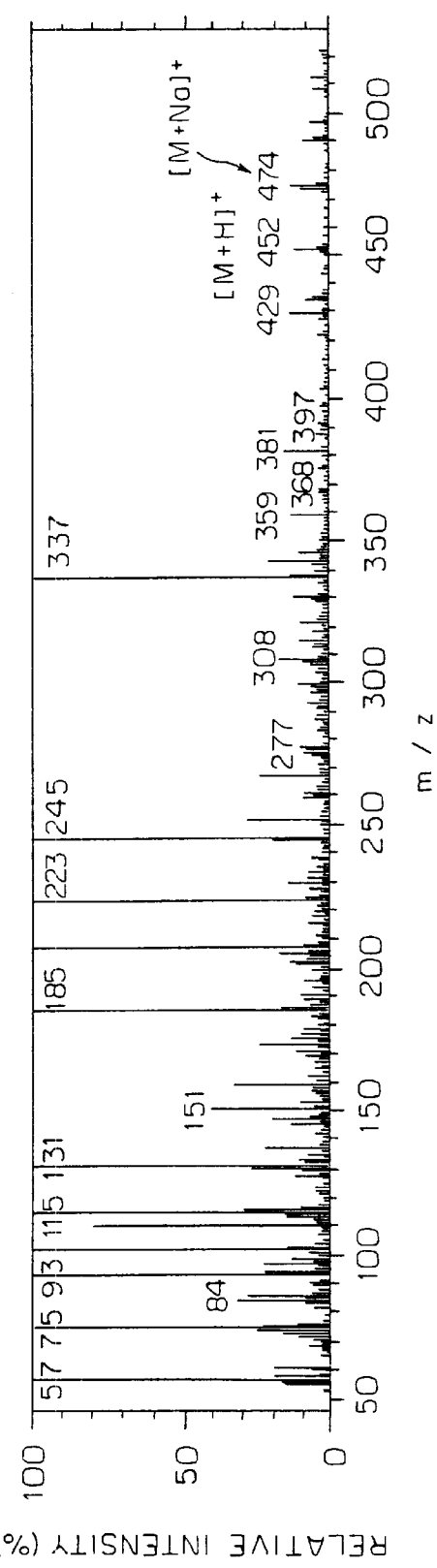
FIG. 7 illustrates the mass spectrum of a product of a reaction between DGE and GSH.
Figure 7B:
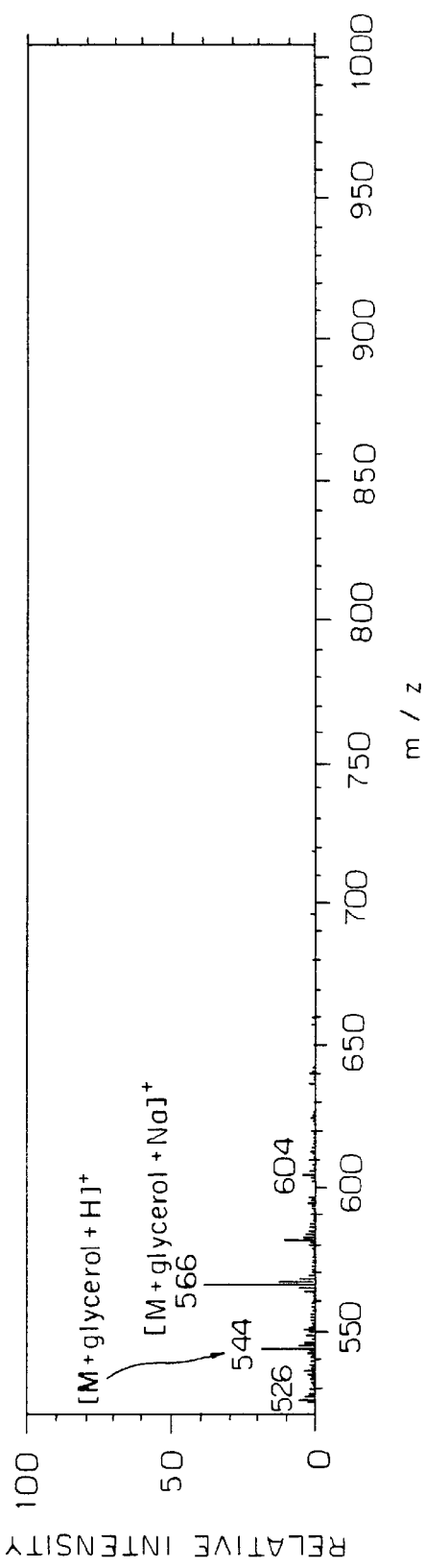
Figure 8:
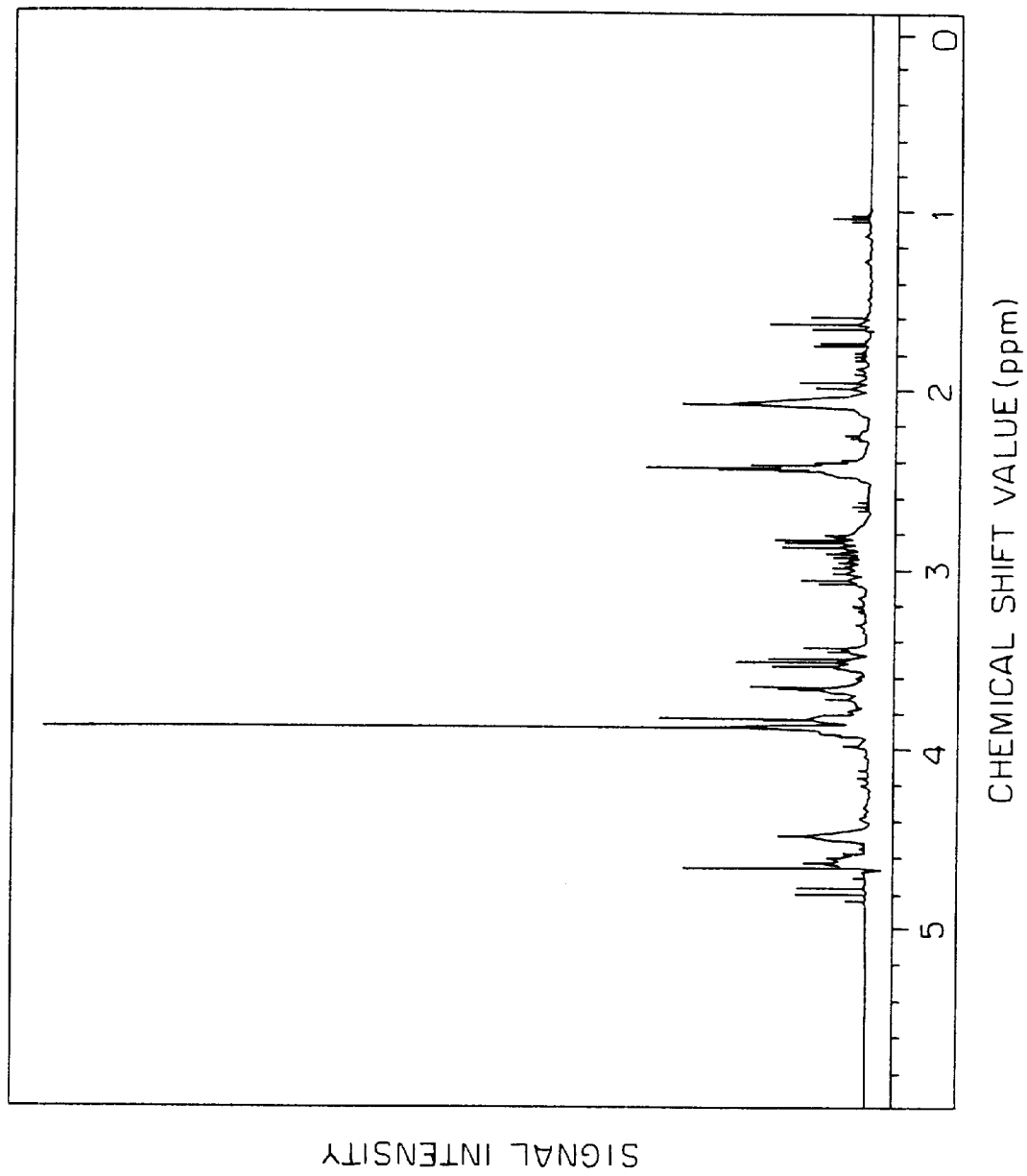
FIG. 8 illustrates the $^1$H-NMR spectrum of a product of a reaction between DGE and GSH.
Figure 9:
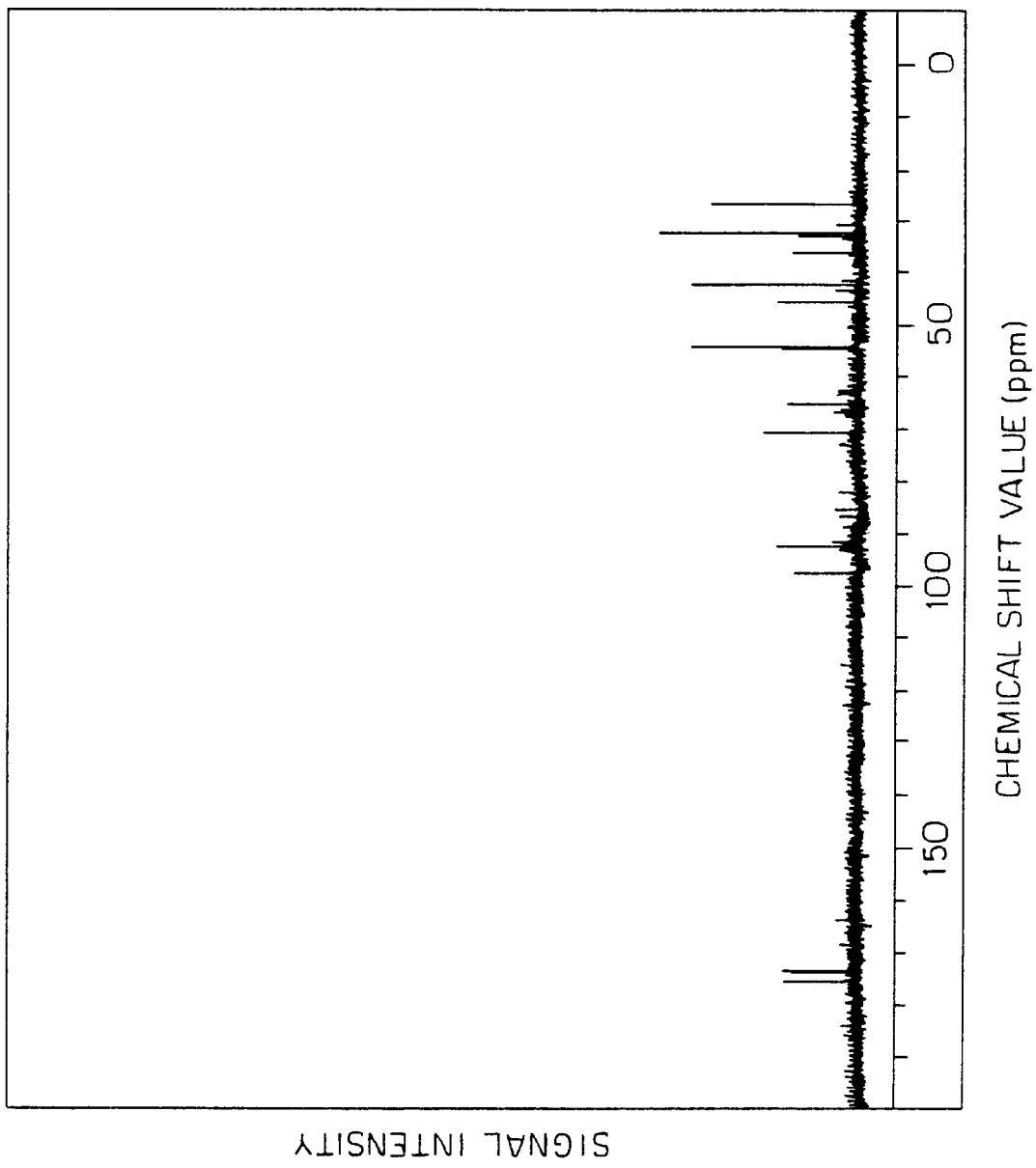
FIG. 9 illustrates the $^{13}$C-NMR spectrum of a product of a reaction between DGE and GSH.

The mass spectrum of an apoptosis-inducing substance obtained in Example 13-(1) is illustrated in FIG. 7. The $^1$H-NMR spectrum of the substance is illustrated in FIG. 8. The $^{13}$C-NMR spectrum of the substance is illustrated in FIG. 9. In FIG. 7, the horizontal axis represents m/z value and the vertical axis represents the relative intensity (%). In FIGS. 8 and 9, the horizontal axes represent the chemical shift value (ppm) and the vertical axes represent the signal intensity.

FAB-MS:m/z
452 [M+H]$^+$
474 [M+Na]$^+$
544 [M+glycerol+H]$^+$
566 [M+glycerol+Na]$^+$ Glycerol was used as a matrix.

$^1$H-NMR: δ1.62 (1H, t, J=13.5 Hz, 6-H), 1.96 (1H, dd, J=4.0, 13.5 Hz, 6-H), 2.07 (2H, m, 5'-H), 2.42 (2H, m, 4'-H), 2.85 (1H, dd, J=8.5, 13.5 Hz, 1'-H), 2.90 (1H, ddd, J=4.0, 10.5, 13.5 Hz, 5-H), 3.06 (1H, dd, J=5.0, 13.5 Hz, 1'-H), 3.44 (1H, dt, J=5.0, 10.5 Hz, 4-H), 3.52 (1H, t, J=10.5 Hz, H-8), 3.66 (1H, dd, J=5.0, 10.5 Hz, H-8), 3.82 (1H, t, J=6.5 Hz, 6'-H), 3.88 (2H, S, 9'-H), 4.47 (1H, dd, J=5.0, 8.5 Hz, 2'-H), 4.65 (1H, S, 2-H)

The chemical shift values in $^1$H-NMR are expressed assuming the chemical shift value of HOD as 4.65 ppm.

$^{13}$C-NMR: δ 26.6 (5'-C), 31.9 (4'-C), 32.7 (1'-C), 35.6 (6-C), 42.0 (9'-C), 45.2 (5-C), 53.9 (6'-C), 54.4 (2'-C), 64.7 (8-C), 70.4 (4-C), 92.1 (2-C), 97.2 (1-C), 173.4 (7'-C), 173.5 (8'-C), 173.8 (10'-C), 175.4 (3'-C)

The chemical shift values in $^1$C-NMR are expressed assuming the chemical shift value of dioxane as 67.4 ppm.

The numbers for peak identification in $^1$H-NMR and $^1$C-NMR are as indicated in the following formula.

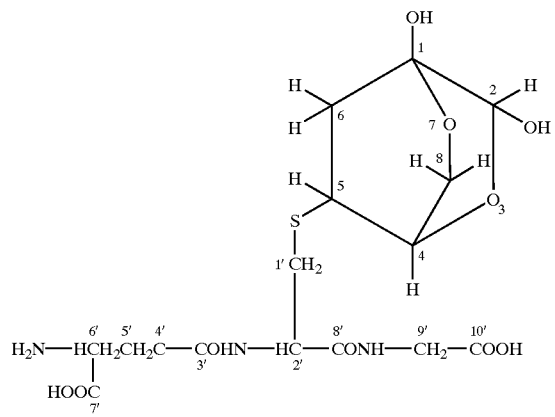

From these results, it revealed that the apoptosis-inducing substance obtained in Example 13-(1) was 5-L-glutathion-S-yl-2-hydroxy-3,7-dioxabicyclo[2.2.2]octan-1-ol (hereinafter simply referred to as DGE-GSH).

EXAMPLE 14

Apoptosis Induction Test

A 10 mg/ml aqueous solution of DGE-GSH obtained in Example 13-(1) was sterilized by filtration and diluted 2-, 4-, 8-, 16-, 32-, 64-, 128-, 256- or 512-folds with sterile water. The antiproliferation activities against HL-60 cells of these dilutions were measured as described in Example 1-(2). As a result, apoptotic bodies were observed for groups to which DGE-GSH was added. The absorbance at 590 nm of these groups was lower than that of the control group to which water was added, indicating the inhibition of cell growth. $GI_{50}$, the concentration that results in 50% growth inhibition as demonstrated by half absorbance at 590 nm as compared with the control group to which water was added, which was calculated based on the above-mentioned results, was about 48.7 µg/ml.

EXAMPLE 15

NO Production Inhibition Test

RAW264.7 cells were suspended in Dulbecco's modified Eagle's medium without phenol red containing 10% fetal bovine serum and 2 mM L-glutamine at a concentration of $3\times10^5$ cells/ml. 500 µl of the suspension was added to each well of a 48-well microtiter plate and the plate was incubated at 37° C. for 12 hours in the presence of 5% $CO_2$. 10 µl of an aqueous solution containing 50 µ/ml lipopolysaccharide and 5000 U/ml interferon-γ, and 10 µl of an aqueous solution prepared by dissolving DGE-GSH prepared in Example 13-(1) in water at a concentration of 1 mM and sterilizing it by filtration were added to the well. The plate was incubated for additional 16 hours. The concentration of $NO_2^-$ produced by oxidation of NO in the medium was then measured. As control groups, a group to which LPS or IFN-γ was not added and a group to which DGE-GSH was not added were provided.

After cultivation, 100 µl of 4% Griess' reagent (Sigma, G4410) was added to 100 µl of the medium, and the mixture was allowed to stand for 15 minutes at room temperature. The absorbance at 490 nm was then measured. $NO_2^-$ concentration in the medium was calculated with reference to a calibration curve prepared by using $NaNO_2$ at a given concentration dissolved in the same medium as that described above.

As a result, the $NO_2^-$ concentration in the medium with no addition was 4.6 µM. The $NO_2^-$ concentration in the control medium to which LPS and IFN-γ were added but DGE-GSH was not added was 12.1 µM. The $NO_2^-$ concentration in the medium to which DGE-GSH was added was low (9.4 µM), indicating the inhibitory effect of DGE-GSH on NO production induced by LPS and IFN-γ.

EXAMPLE 16

Prostaglandin $E_2$ Production Inhibition Test

RAW264.7 cells were suspended in Dulbecco's modified Eagle's medium without phenol red containing 10% fetal bovine serum and 2 mM L-glutamine at a concentration of $3\times10^5$ cells/ml. 500 µl of the suspension was added to each well of a 48-well microtiter plate and the plate was incubated at 37° C. for 12 hours in the presence of 5% $CO_2$. 10 µl of 50 µg/ml aqueous lipoplysaccharide solution and 10 µl of an aqueous solution prepared by dissolving DGE-GSH prepared in Example 13-(1) at a concentration of 1 mM in water and sterilizing it by filtration were then added to the well. After the plate was incubated for additional 16 hours, the amount of prostaglandin $E_2$ was measured. As control groups, a group to which LPS was not added and a group to which DGE-GSH was not added were provided.

After cultivation, the amount of prostaglandin $E_2$ in the culture supernatant was measured using Prostaglandin $E_2$ ELISA Kit (Neogen, Code. 404110).

As a result, the prostaglandin $E_2$ concentration in the medium with no addition was 50.3 ng/ml. The prostaglandin $E_2$ concentration in the control medium to which LPS was added but DGE-GSH was not added was 63.4 ng/ml. The prostaglandin $E_2$ concentration in the medium to which DGE-GSH was added was low (50.7 ng/ml), indicating the inhibitory effect of DGE-GSH on prostaglandin $E_2$ production induced by LPS.

EXAMPLE 17

Lymphocyte Activation Inhibition Test

A ddY mouse (female, 7 weeks old, weighing about 25 g) was purchased from Nippon SLC and pre-bred for 1 week before using in experiments. A spleen was taken out from the mouse, finely minced and suspended in RPMI-1640 medium containing 10% fetal bovine serum (HyClone) to obtain a single cell suspension. Adhesive cells adhered to a plastic Petri dish were removed and non-adhesive cells were used as spleen lymphocytes. The spleen lymphocytes were suspended in RPMI 1640 medium containing 10% fetal bovine serum at a concentration of $2\times10^6$/ml. 200 µl of the suspension was seeded into each well of a 96-well microtiter plate. DGE at a varying concentration was added to each well other than the control well. Furthermore, 5 µg of Con A (Nacalai Tesque) was added to each well. The plate was incubated at 37° C. for two days in the presence of 5% $CO_2$. 37 kBq of $^3$H-thymidine (Daiichi Pure Chemicals) was added to each well to pulse-label the cells on the day before the completion of the cultivation. After cultivation, the cells were harvested on a glass filter to measure the radioactivity.

Figure 10:
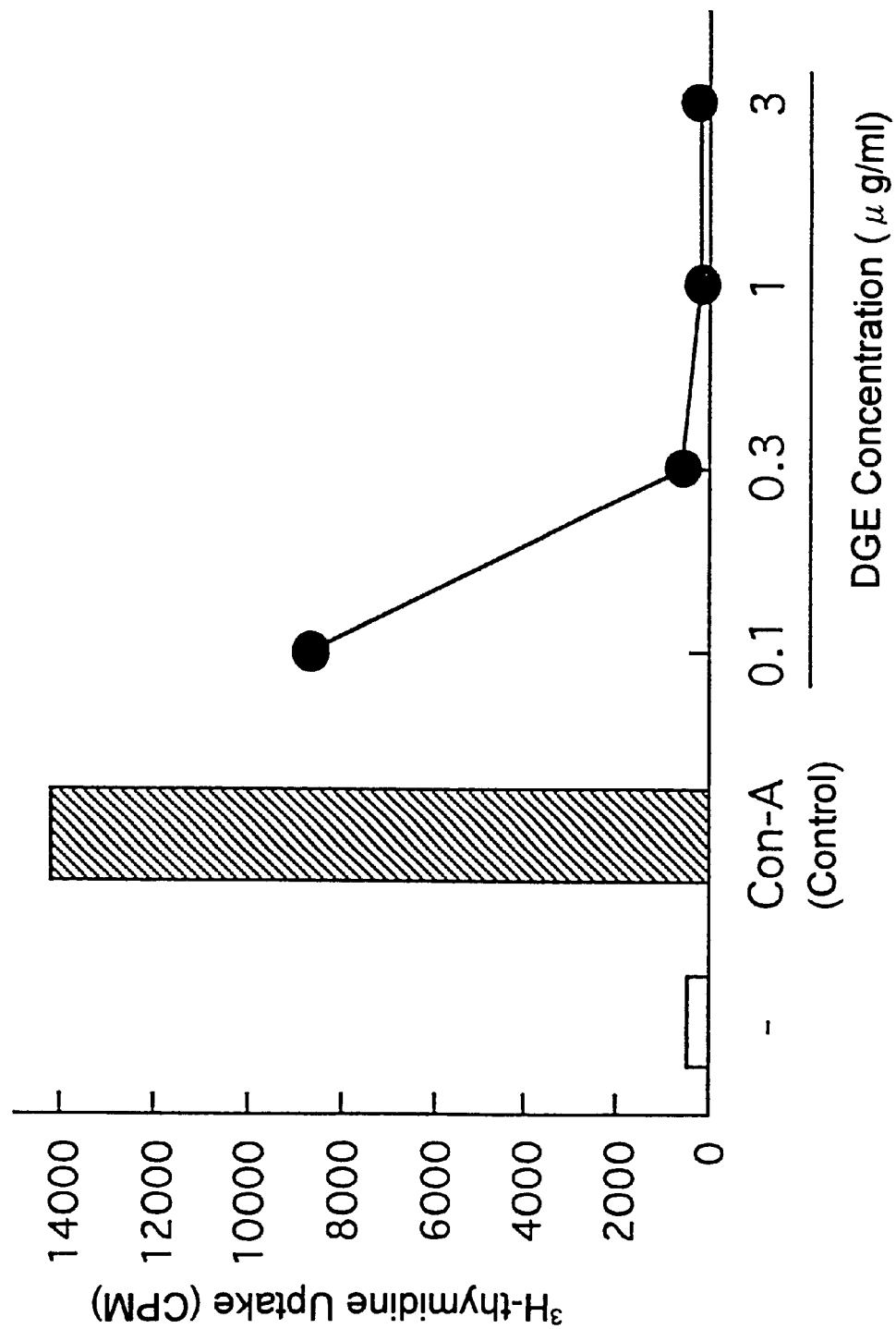
FIG. 10 illustrates the $^3$H-thymidine uptake when cultured in the presence of DGE.

The results are shown in FIG. 10. DGE exhibited an inhibitory activity against lymphocyte proliferation activated by stimulation with mitogen in a dose-dependent manner, and almost completely inhibits the proliferation at a concentration of 0.3 µg/ml. Thus, the inhibitory activity of DGE against lymphocyte activation has been demonstrated.

As described above, the present invention provides a compound of formula (I), a compound of formula (II), salts thereof and an apoptosis-inducing substance of the present invention useful as an active ingredient of a composition for inducing apoptosis, a carcinostatic composition, antioxidant compositions such as a composition for inhibiting active oxygen production, a composition for inhibiting lipid peroxide radical production and a composition for inhibiting NO production, a composition for inhibiting prostaglandin synthesis, an anti-pathogenic microbial composition, a composition for preserving freshness, an antimutagenic composition, an anti-hyperglycemic composition, an anti-hyperlipidemic composition, a composition for inducing heat shock protein production, an antiviral composition and a composition for inhibiting α-glycosidase.

Foods or drinks which contain, which are produced by diluting, and/or which are produced by adding thereto such substances are useful as functional foods or drinks that have an apoptosis-inducing activity, a carcinostatic activity, antioxidant activities such as an activity of inhibiting active oxygen production and an activity of inhibiting NO production, an activity inhibiting prostaglandin synthesis, an anti-pathogenic microbial activity, an antimutagenic activity, an anti-hyperglycemic activity, an anti-obese activity, an activity of inducing heat shock protein production and an antiviral activity. Thus, the present invention provides foods or drinks which induce apoptosis in cells in lesions in patients with cancers or viral diseases and, therefor, are effective in preventing or ameliorating the disease states of these diseases. Apoptosis can be induced in tumor cells upon oral intake of the above-mentioned compounds of the present invention in foods or drinks. Therefore, in case of cancers of digestive organs such as colon cancer and stomach cancer, among others, the foods or drinks of the present invention have excellent effects of preventing or ameliorating the disease state of cancers of digestive organs. Furthermore, the above-mentioned foods or drinks are excellent as anti-oxidative stress foods or drinks based on their antioxidant activities such as the activity of inhibiting the active oxygen production.

In addition, the compounds of formula (I) or formula (II) are also useful as compounds for antioxidation for inhibition of active oxygen production. The foods or drinks containing, produced by diluting and/or produced by adding thereto the compound for antioxidation of the present invention is useful as those for ameliorating the disease states of diseases due to oxidizing substances in a living body such as active oxygen. Furthermore, the foods or drinks of the present invention are effective for amelioration or prevention of constipation.

The compound of formula (I), the compound of formula (II) and salts thereof provided by the present invention are useful as novel functional compounds which provide antioxidant activities such as an activity of inhibiting active oxygen production to foods or drinks.

The compounds of the present invention have an activity of preserving freshness. Therefore, they are very useful for keeping taste and freshness of foods or perishables.

Furthermore, the cosmetic compositions containing the compounds of the present invention are useful as those for whitening or moisturizing.

What is claimed is:

1. A pharmaceutical composition which contains as an active ingredient a compound selected from the group consisting of:

a compound of formula (I):

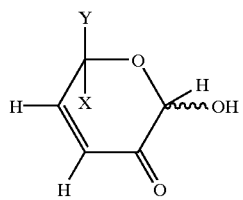

(I)

wherein X and Y are H or CH$_2$OH, provided that when X is CH$_2$OH, Y is H, while when X is H, Y is CH$_2$OH;
a compound of formula (II):

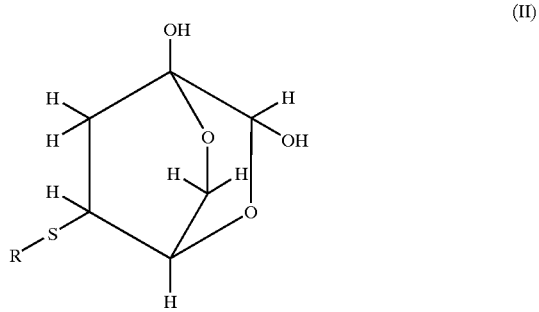

(II)

wherein R is a residue obtained by freeing an SH group from an SH group-containing compound; and salts thereof.

2. A method for producing a compound of formula (I) defined by claim 1, characterized in that the method comprises treating one or both of 3,6-anhydrogalacrose and a compound having 3,6-anhydrogalactose at its reducing end under neutral to alkaline conditions.

3. The method according to claim 2, wherein said one or both of 3,6-anhydrogalactose and the compound having 3,6-anhydrogalactose at its reducing end is obtained by hydrolysis under acidic conditions or enzymatic digestion of a 3,6-anhydrogalactose-containing material.

4. The method according to claim 3, wherein the compound having 3,6-anhydrogalactose at its reducing end is at least one compound selected from the group consisting of agarobiose, κ-carabiose and a compound other than agarobiose and κ-carabiose having 3,6-anhydrogalactose at its reducing end.

5. The method according to claim 3, wherein the 3,6-arnhydrogalactose-containing material is agar, agarose, carrageenan or a mixture of two or more thereof.

6. A compound of formula (II) or a salt thereof defined by claim 1.

7. A method for producing a compound of formula (II), characterized in that the method comprises reacting a compound of formula (I) defined by claim 1 with an SH group-containing compound.

8. A food or a drink which contains, which is produced by diluting, or which is produced by adding thereto a compound selected from the group consisting of a compound of formula (I), a compound of formula (II) and salts thereof defined by claim 1.

9. A food or a drink which contains, which is produced by diluting, or which is produced by adding thereto a compound of formula (I) defined by claim 1 obtained by treating one or both of 3,6-anhydrogalactose and a compound having 3,6-anhydrogalactose at its reducing end under neutral to alkaline conditions.

10. The food or the drink according to claim 9, wherein at least one of said 3,6-anhydrogalactose and the compound having 3,6-anhydrogalactose at its reducing end is obtained by hydrolysis under acidic conditions or enzymatic digestion of a 3,6-anhydrogalactose-containing material.

11. The food or the drink according to claim 10, wherein the compound having 3,6-anhydrogalactose at its reducing end is at least one compound selected from the group consisting of agarobiose, κ-carabiose and a compound other than agarobiose and κ-carabiose having 3,6-anhydrogalactose at its reducing end.

12. The food or the drink according to claim 10, wherein the 3,6-anhydroqalactose-containing material is agar, agarose, carrageenan, or a mixture of two or more thereof.

13. An antioxidant composition which contains as an active ingredient a compound selected from the group consisting of a compound of formula (I), a compound of formula (II) and salts thereof defined by claim 1.

14. The antioxidant composition according to claim 13, which is a composition for inhibiting active oxygen production.

15. A food or a drink which contains the antioxidant composition according to claim 13.

16. A compound for antioxidation of formula (I) or formula (II) defined by claim 1.

17. The compound according to claim 16, which is a compound for inhibiting active oxygen production.

18. A composition for preserving freshness which contains as an active ingredient a compound selected from the group consisting of a compound of formula (I), a compound of formula (II) and salts thereof defined by claim 1.

19. A cosmetic composition which contains as an active ingredient a compound selected from the group consisting of a compound of formula (I), a compound of formula (II) and salts thereof defined by claim 1.

20. A composition for inhibiting α-glycosidase which contains as an active ingredient a compound selected from the group consisting of a compound of formula (I), a compound of formula (II) and salts thereof defined by claim 1.

21. An apoptosis-inducing substance produced by treating at least one of 3,6-anhydrogalactose and a compound having 3,6-anhydragalactose at its reducing end under neutral to alkaline conditions.

22. The substance according to claim 21, wherein the compound having 3,6-anhydrogalactose at its reducing end is at least one compound selected from the group consisting of agarobiose, κ-carabiose and a compound other than agarobiose and κ-carabiose having 3,6-anhydrogalactose at its reducing end.

23. A food or a drink which contains, which is produced by diluting, or which is produced by adding thereto an apoptosis-inducing substance produced by treating at least one of 3,6-anhydrogalactose and a compound having 3,6-anhydrogalactose at its reducing end under neutral to alkaline conditions.

* * * * *